US008101357B2

(12) United States Patent
Yaku et al.

(10) Patent No.: US 8,101,357 B2
(45) Date of Patent: Jan. 24, 2012

(54) METHOD FOR INHIBITING TELOMERASE REACTION USING AN ANIONIC PHTHALOCYANINE COMPOUND

(75) Inventors: Hidenobu Yaku, Osaka (JP); Daisuke Miyoshi, Hyogo (JP)

(73) Assignee: Panasonic Corporation, Osaka (JP)

(*) Notice: Subject to any disclaimer, the term of this patent is extended or adjusted under 35 U.S.C. 154(b) by 0 days.

(21) Appl. No.: 12/710,837

(22) Filed: Feb. 23, 2010

(65) Prior Publication Data

US 2010/0261246 A1    Oct. 14, 2010

Related U.S. Application Data

(63) Continuation of application No. PCT/JP2009/003232, filed on Jul. 10, 2009.

(30) Foreign Application Priority Data

Apr. 9, 2009   (JP) .................................. 2009-094788

(51) Int. Cl.
*C12Q 1/68* (2006.01)
(52) U.S. Cl. ....................................................... 435/6.1
(58) Field of Classification Search .................. None
See application file for complete search history.

(56) References Cited

U.S. PATENT DOCUMENTS

| | | | |
|---|---|---|---|
| 6,087,493 A * | 7/2000 | Wheelhouse et al. | ........ 540/145 |
| 7,144,879 B2 | 12/2006 | Roncucci et al. | |
| 7,432,369 B2 | 10/2008 | Williams et al. | |
| 2003/0170178 A1 | 9/2003 | Roncucci et al. | |
| 2004/0029855 A1 | 2/2004 | Klaveness et al. | |
| 2004/0034023 A1 | 2/2004 | Mergny et al. | |
| 2006/0003982 A1 | 1/2006 | Williams et al. | |
| 2007/0066513 A1 | 3/2007 | Roncucci et al. | |
| 2007/0232572 A1 | 10/2007 | Hittinger et al. | |
| 2008/0009473 A1 | 1/2008 | Williams et al. | |
| 2009/0215105 A1 | 8/2009 | Hammer et al. | |

FOREIGN PATENT DOCUMENTS

| | | |
|---|---|---|
| EP | 1 164 135 A1 | 12/2001 |
| JP | 2004-505082 | 2/2004 |
| JP | 2005-289874 | 10/2005 |
| JP | 2006-518726 | 8/2006 |
| WO | WO 02/09690 A2 | 2/2002 |
| WO | WO 2005/097123 A2 | 10/2005 |
| WO | WO 2007/009101 A2 | 1/2007 |
| WO | WO 2007 090343 A1 * | 8/2007 |

OTHER PUBLICATIONS

Gill, Excerpts from Dissertation, Insights into Sulfonated Phthalocyanines; Insights into Anionic Tetraaryl Porphyrins; Irradiation of Cationic Metalloporphyrins Bound to DNA, Georgia University, Dec. 4, 2006, 12 total pages, pp. 9-12 of Dissertation body.*

Akatov, V.S., et al., "Apoptic Death of Human Lympholeukemia HL-60 Cells Resultant from Combined Effect of Cobalt Octa-4,5-Carboxyphthalocyanine Propylenglycol Ether and Ascorbate", Bulletin of Experimental Biology and Medicine, Dec. 2005, pp. 729-732, vol. 140 No. 6, Springer Science + Business Media, Inc.

Shi, D-F, et al., "Quadruplex-Interactive Agents as Telomerase Inhibitors: Synthesis of Porphyrins and Structure—Activity Relationship for the Inhibition of Telomerase", J. Med. Chem., 2001, pp. 4509-4523, vol. 44, American Chemical Society.

Wheelhouse, R. T., et al., "Cationic Porphyrins as Telomerase Inhibitors: the Interaction of Tetra-(N-methyl-4-pyridyl) porphine with Quadruplex DNA", Journal of the American Chemical Society, 1998, pp. 3261-3262, vol. 120, American Chemical Society.

Cian, A., et al., "Highly Efficient G-Quadruplex Recognition by Bisquinolinium Compounds", Journal of the American Chemical Society, 2007, pp. 1856-1587, vol. 129 No. 7, American Chemical Society.

Arthanari, H., et al., "Fluorescent dyes specific for quadruplex DNA", Nucleic Acids Research, 1998, vol. 26, No. 16, pp. 3724-3728, Oxford University Press.

Ren, J., et al., "Sequence and Structural Selectivity of Nucleic Acid Binding Ligands", Biochemistry, 1999, pp. 16067-16075, vol. 38, American Chemical Society.

Monchaud, D., et al., "A hitchhiker's guide to G-quadruplex ligands", Organic & Biomolecular Chemistry, 2008, pp. 627-636, The Royal Society of Chemistry.

Huang, Z., et al., "G-Quadruplexes: Targets in Anticancer Drug Design", ChemMedChem, 2008, pp. 690-713, vol. 3.

Kim, M-Y., et al., "Telomestatin, a potent Telomerase Inhibitor That Interacts Quite Specifically with the Human Telomeric Intramolecular G-Quadruplex", J. Am. Chem. Soc., 2002, pp. 2098-2099, vol. 124 No. 10, American Chemical Society.

Pennarun, G., et al, "Apoptosis related to telomere instability and cell cycle alterations in human glioma cells treated by new highly selective G-quadruplex ligands", Oncogene, 2005, pp. 2917-2928, vol. 24, Nature Publishing Group.

Zhang, L., et al., "Synthesis and evaluation of cationic phthalocyanine derivatives as potential inhibitors of telomerase", Bioorganic & Medicinal Chemistry, 2008, pp. 303-312, vol. 16, Elsevier.

English translation of K. Shinohara et al., "Inhibiting of Telomerase with G-Quadruplex Molecules," Chemical Biology, 2005, pp. 68-69, vol. 60, No. 7.

* cited by examiner

Primary Examiner — Christopher M. Babic

(74) Attorney, Agent, or Firm — McDermott Will & Emery LLP

(57) ABSTRACT

An object of the present invention is to provide a method for inhibiting a DNA extension reaction by telomerase.

More specifically, the present invention relates to a method for inhibiting a DNA extension reaction by telomerase, the method being characterized by including the step of adding an anionic phthalocyanine to a solution containing telomerase, a DNA to be a substrate of a telomerase reaction, and dNTPs.

3 Claims, 21 Drawing Sheets

In vitro (a)
DNA to be a substrate of
a telomerase reaction
(TS primer, etc.)

Telomerase

+ ◯ + dNTP

Telomerase reaction occurs.

Sequence elongated by the telomerase reaction (b)
DNA to be a substrate of
a telomerase reaction
(TS primer, etc.)

Telomerase

+ ◯ + dNTP + Anionic phthalocyanine

Telomerase reaction is suppressed.

Human cell (a)

(b)

(A)

(B)

(A)

(B)

(A)

(B)

METHOD FOR INHIBITING TELOMERASE REACTION USING AN ANIONIC PHTHALOCYANINE COMPOUND

This is a continuation application under U.S.C 111(a) of pending prior International application No. PCT/JP2009/003232, filed on Jul. 10, 2009, which in turn claims the benefit of Japanese Application No. 2009-94788 filed on Apr. 9, 2008, the disclosures of which Application are incorporated by reference herein.

TECHNICAL FIELD

The present invention relates to a method for inhibiting a DNA extension reaction by telomerase.

BACKGROUND ART

Telomere has a structure composed of DNAs and several proteins located at both ends of chromosomes of eucaryotic organisms. In the case of human, the DNA in the telomere portion (hereinafter, may be merely referred to as "telomeric DNA") exists as approximately 10,000 base pairs which include repeating sequences of six bases, i.e., 5'-TTAGGG-3' (SEQ ID NO: 1), and the 3'-end is overhang and forming a single strand of about 100 bases.

According to researches carried out so far, it has been known that telomeric DNAs in normal somatic cells are shortened with every cell division, and when the telomeric DNAs are shortened to approximately 5,000 base pairs, the cells reach the limit of replicative senescence and then the cells which are not capable of division are finally induced to apoptosis.

On the other hand, it has been elucidated that since the activity of telomerase that allows the shortened telomeric DNAs to elongate again is very high in 70 to 80% of cancer cells, the cells do not reach the replicative senescence and thus keep dividing. Therefore, the extension reaction of telomeric DNAs by telomerase (hereinafter, maybe merely referred to as "telomerase reaction") has been considered as an important target in treatment of cancer in recent years, and inhibitors and inhibition methods of this reaction have been extensively investigated.

Various methods for inhibiting a telomerase reaction have been proposed, including inhibition methods by stabilization of a G-quadruplex structure. G-quadruplex structure is a quadruplex DNA structure formed with a DNA sequence that is rich in guanine bases, and the single strand portion of the telomeric DNA sequence (5'-TTAGGG-3'; SEQ ID NO: 1) is also a sequence capable of forming the G-quadruplex structure.

Since telomerase is not capable of binding to a G-quadruplex structure, the telomerase reaction can be inhibited when stable existence of the G-quadruplex structure is enabled in a telomeric DNA. In this respect, methods for inhibiting a telomerase reaction via stabilization of a G-quadruplex structure by various compounds have been proposed hitherto.

PTL 1 reports an effect of inhibiting a telomerase reaction by pyrazolone derivatives. PTL 2 reports an effect of inhibiting a telomerase reaction by compounds represented by the general formula: nitrogen-containing aromatic ring having a quaternary nitrogen atom-(NR3)p-CO-partitioning agent-(CO)m-(NR'3)q-X-an aromatic ring or a non-aromatic ring. In addition, PTL 3 reports an effect of inhibiting a telomerase reaction by compounds having structures represented by the following chemical formula 1.

[Chemical formula 1]

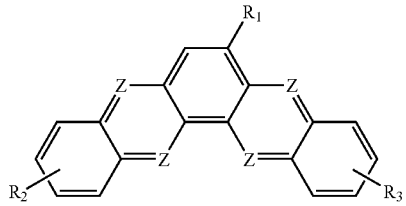

NPL 1, NPL 2 and NPL 3 each report effects of inhibiting a telomerase reaction by Telomestatin, Phen-DC3 and 360A. Furthermore, NPL 4 reports an effect of inhibiting a telomerase reaction by TMPyP4. In addition, similar inhibitory effects by a perylene derivative, or quinoline and quinoline-related substances have been also reported.

CITATION LIST

[Patent Literature]
PTL 1: Japanese Patent Laid-open Publication No. 2005-289874
PTL 2: Japanese Patent Laid-open Publication No. 2006-518726
PTL 3: Japanese Patent Laid-open Publication No. 2004-505082

[Nonpatent Literature]
NPL 1: J. Am. Chem. Soc. (2002) 124, 2098-2099
NPL 2: J. Am. Chem. Soc. (2007) 129, 1856-1857
NPL 3: Oncogene (2005) 24, 2917-2928
NPL 4: J. Am. Chem. Soc. (1998) 120, 3261-3262

SUMMARY OF INVENTION

Problems to be Solved by the Present Invention

What is the most important for the compounds relating to the inhibition of a telomerase reaction described above involves the point that they do not interact with a double-stranded DNA structure, but have to bind specifically to a G-quadruplex structure.

The reason is that most genomic DNAs have a double helix structure, and nonspecific interaction of these compounds to genomic DNAs leads to cell toxicity. More specifically, non-specific binding of these compounds also to a double-stranded DNA structure will result in inhibition of also a DNA extension reaction by a polymerase required for replication of the DNA.

Any compounds which have been developed for the purpose of inhibiting a telomerase reaction by stabilization of a G-quadruplex structure are either electrically neutral or cationic. Because DNA itself is anionic, and thus electrostatic repulsion may occur with anionic compounds, which can be disadvantageous in binding reactions from the viewpoint of allowing for binding to the G-quadruplex. Therefore, in attempts to achieve inhibition of a telomerase reaction by stabilization of a G-quadruplex structure, the use of an anionic compound has not been conceived.

The present inventors elaborately investigated under such circumstances, and consequently discovered that anionic phthalocyanines specifically interact with a G-quadruplex structure and have superior effects of inhibiting a telomerase reaction. Accordingly, the present invention was accomplished.

Means for Solving the Problems

One aspect of the present invention for solving the foregoing problems relates to a method for inhibiting a DNA extension reaction by telomerase, being a method for inhibiting a telomerase reaction, characterized in that an anionic phthalocyanine as a telomerase inhibitor is allowed to react with a DNA to be a substrate of telomerase.

Specifically, in the method of inhibiting a telomerase reaction according to one aspect of the present invention, an anionic phthalocyanine is add to a solution (a buffer solution in many cases) containing telomerase, a DNA to be a substrate of a telomerase reaction, and dNTPs.

The anionic phthalocyanine preferably has at least one functional group selected from the group consisting of a carboxyl group, a metal salt of a carboxyl group, a sulfo group, and a metal salt of a sulfo group.

The anionic phthalocyanine is preferably either an anionic phthalocyanine coordinated with at least one metal selected from the group consisting of copper, zinc, cobalt and nickel, or an anionic phthalocyanine without a coordinated metal.

The aforementioned objects, other objects, features, and advantages of the present invention are clarified by the following detailed description of preferred embodiments with reference to accompanying drawings.

Advantageous Effects of Invention

According to the present invention, a method capable of inhibiting a telomerase reaction through a specific interaction with a G-quadruplex structure without nonspecific binding of a compound to a DNA having a double helix structure is provided.

DESCRIPTION OF EMBODIMENTS

Hereinafter, Embodiments according to the present invention are explained with appropriate reference to accompanying drawings.

Figure 1:
FIG. 1 shows an explanatory view for illustrating an embodiment (in vitro) of the present invention.
Figure 1:
Figure 1:
Figure 1:
Figure 1:
Figure 1:
Figure 1:

First, as one example of the embodiment of the present invention, a method of inhibiting a telomerase reaction by an anionic phthalocyanine in vitro is explained with reference to FIG. 1.

As shown in FIG. 1(a), a telomerase reaction firstly occurs in a solution containing telomerase, a DNA to be a substrate of telomerase and dNTPs. Accordingly, the DNA to be a substrate of telomerase is elongated in the 3' direction with repeating telomeric DNAs.

On the other hand, as demonstrated by Examples described in the following, the telomerase reaction is inhibited when an anionic phthalocyanine is further added in the solution containing telomerase, a DNA to be a substrate of telomerase, and dNTPs, as shown in FIG. 1(b). This makes the basis of the principle of the present invention.

Examples of the "DNA to be a substrate of telomerase" herein include e.g., TS primers and the telomeric DNA (SEQ ID NO: 1).

The term "dNTPs" as used herein means a mixture of four kinds of deoxyribonucleoside triphosphate (dATP, dCTP, dGTP, and dTTP). However, since the telomeric DNA (SEQ ID NO: 1) does not have C (cytosine), dCTP is not necessarily included in "dNTPs". It should be noted that dATP represents deoxyadenosine triphosphate, dCTP represents deoxycytidine triphosphate, dGTP represents deoxyguanosine triphosphate, and dTTP represents deoxythymidine triphosphate.

Figure 2:
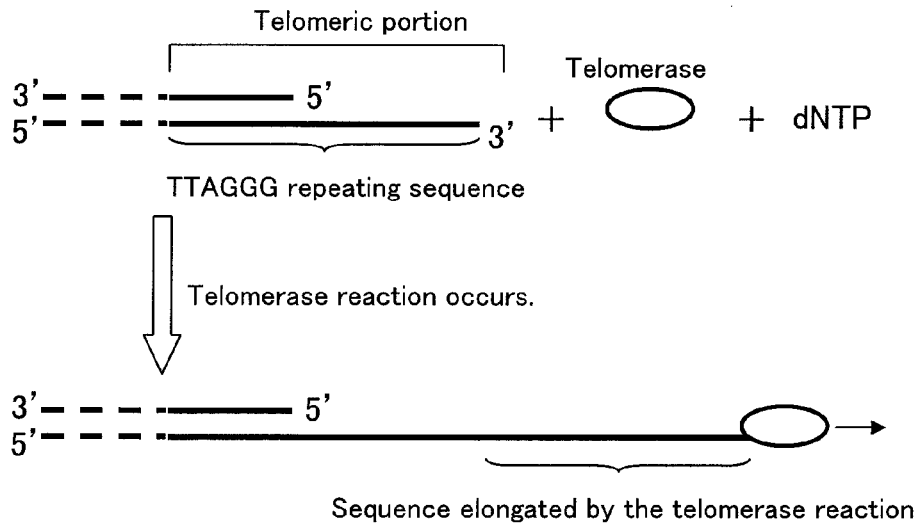
FIG. 2 shows an explanatory view for illustrating another embodiment (in vivo (in human cells)) of the present invention.
Figure 2:
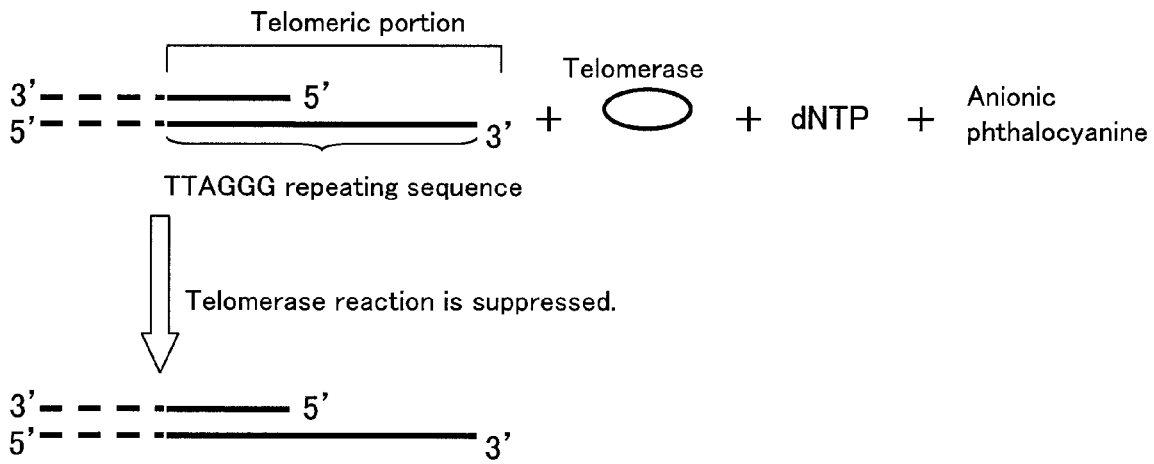

Next, as one example of the embodiment of the present invention, a method of inhibiting a telomerase reaction by an anionic phthalocyanine in vivo (in human cells) is explained with reference to FIG. 2. As shown in FIG. 2(a), telomere portions at the end of a duplex DNA included in cells are constructed with repeating sequences of the telomeric DNA: 5'-TTAGGG-3' (SEQ ID NO: 1) in vivo. Thus, a telomerase reaction occurs as long as such a telomere portion, telomerase and dNTPs are present.

However, as shown in FIG. 2(b), the intracellular telomerase reaction is inhibited when an anionic phthalocyanine is present.

Figure 3:
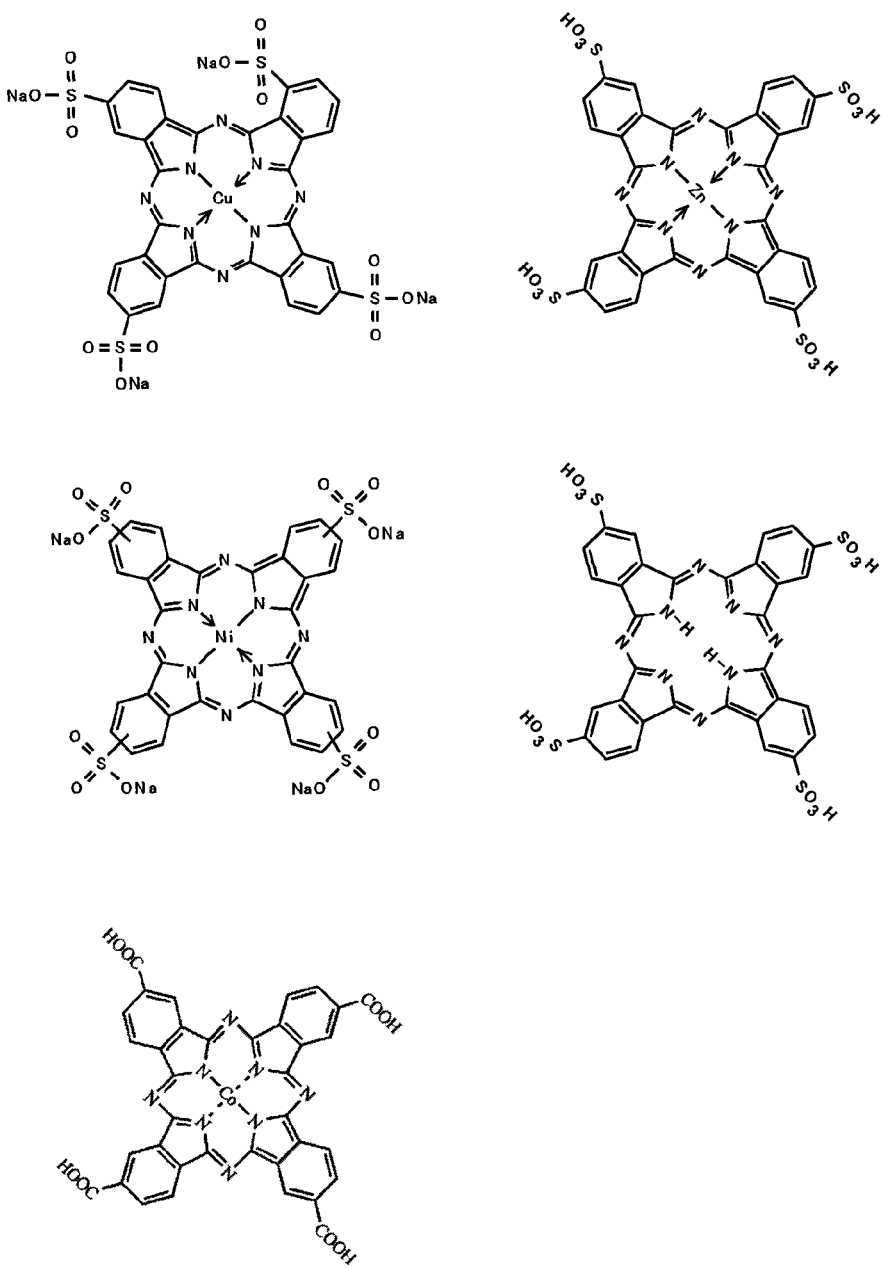
FIG. 3 shows a view for illustrating examples of anionic phthalocyanines used in an embodiment of the present invention.

The anionic phthalocyanine according to embodiments of the present invention is preferably any one of anionic phthalocyanines coordinated with at least one metal selected from the group consisting of copper, zinc, cobalt and nickel, or an anionic phthalocyanine without a coordinated metal, as shown in FIG. 3. In addition, the anionic phthalocyanine according to embodiments of the present invention preferably has as a functional group at least one obtained from the group consisting of a carboxyl group, a metal salt of a carboxyl group, a sulfo group, and a metal salt of a sulfo group, as shown in FIG. 3.

EXAMPLES

Among phthalocyanines used in the following Examples, Copper(II) phthalocyanine-3,4',4",4"'-tetrasulfonic acid tetrasodium salt (hereinafter, merely referred to as CuPC) and Nickel(II) phthalocyanine tetrasulfonic acid tetrasodium salt (hereinafter, merely referred to as NiPC) were purchased from Sigma-Aldrich Corporation. Phthalocyanine tetrasulfonic acid (hereinafter, merely referred to as PC) and Zinc(II) phthalocyanine tetrasulfonic acid (hereinafter, merely referred to as ZnPC) were purchased from Funakoshi Co., Ltd. TMPyP was purchased from Dojindo Laboratories. Cobalt(II) phthalocyanine tetracarboxylic acid (hereinafter, merely referred to as CoPC) was synthesized by the present inventors. The synthetic method is as follows.

Trimellitic acid in an amount of 6.4 g, 20 g of urea, 4.75 g of cobalt chloride hexahydrate and 0.82 g of ammonium molybdate tetrahydrate were heated in 100 mL of nitrobenzene in an oil bath of 170 to 180° C. for 4.5 hrs. After standing to cool, decantation was carried out to remove the nitrobenzene layer. The residual matter was washed with methanol and water, and dried in a vacuum to obtain 8.66 g of a solid. This solid in an amount of 1.0 g in 30 g of a 50% aqueous potassium hydroxide solution, was stirred at 70 to 75° C. for 2 hrs, and 90 mL of water was added thereto, followed by stirring and filtration. Thus obtained filtrate was strongly acidified with 35 to 37% hydrochloric acid to allow for deposition of precipitate, which was collected by filtration. The precipitate was dissolved in 100 mL of 1 N aqueous sodium hydroxide solution, and filtrated again. Thus obtained filtrate was strongly acidified with hydrochloric acid again, and the deposited precipitate was collected by filtration. After the precipitate was washed with a large quantity of water, drying in vacuum gave CoPC as 0.1 g of a powder. CoPC used in Examples below was obtained by such a synthesis process.

—Study on Inhibitory Effect on Telomerase Activity by Anionic Phthalocyanine—

Comparative Examples 1 and 2, and Examples 1, 2 and 3 are described in the following. In this experiment, comparative studies of effects of inhibiting telomerase by an anionic phthalocyanine and cationic porphyrin (TMPyP) that is a conventionally known typical material having an effect of inhibiting telomerase were carried out using a kit for telomerase activity measurement manufactured by Millipore Corporation (TRAPEZE Telomeraze Detection Kit S7700).

TRAPEZE Telomeraze Detection Kit S7700 (hereinafter, merely referred to as S7700 kit) is a kit that includes 10×TRAP Reaction buffer, 50×dNTPs Mix, TS primer, Primer Mix, and a control cell pellet.

Here, the TRAP Reaction buffer is a buffer solution for permitting the reaction using the S7700 kit.

The dNTP Mix is a liquid mixture of dATP, dCTP, dGTP and dTTP.

The control cell pellet is a pellet of cells including telomerase, and this enables a solution containing telomerase to be prepared.

The TS primer is an oligo DNA consisting of 5'-AATC-CGTCGAGCAGAGTT-3', and serves as an initiation sequence of the telomerase reaction upon binding of telomerase, similarly to a human telomeric DNA sequence.

Essentially, it may be desired that the amount of the reaction product of the telomerase reaction initiated from this TS primer can be directly determined. However, since the amount of this product is very little, the detection with electrophoresis is impossible, and thus it is necessary to amplify the obtained telomerase reaction product by PCR.

Therefore, the Primer Mix in the S7700 kit includes RP primer. This primer is an oligo DNA having a sequence complementary to the sequence elongated by the telomerase reaction, and thus, the telomerase reaction product can be amplified to a detectable level on electrophoresis by carrying out PCR using the aforementioned TS primer and the RP primer.

Although PCR requires a heat resistant polymerase, the S7700 kit does not include it. Therefore, TITANIUM Taxa polymerase (manufactured by Clontech Laboratories) was used in the present studies.

As described above, the telomerase reaction and PCR are carried out sequentially in the telomerase activity measurement using the S7700 kit.

In practice, as described in detail for Comparative Examples 1 to 2 and Examples 1 to 3, necessary reagents are all mixed first, and the telomerase reaction and PCR are carried out sequentially by regulating the temperature of this reaction solution.

In such a procedure, materials expected to inhibit the telomerase reaction (TMPyP and anionic phthalocyanine in the present experiment) are also mixed in the first step. Then, detection of the telomerase reaction product may be confirmed on the basis of the results of electrophoresis carried out in the final step.

However, it should be noted that even though the telomerase reaction product was not detected in the results of electrophoresis, it is unclear that the material expected to inhibit the telomerase reaction inhibited the telomerase reaction in a practical sense.

More specifically, it is probable that the telomerase reaction was not inhibited, whereas the following PCR was inhibited.

For example, it is highly probable that materials which nonspecifically bind to double-stranded DNAs inhibit PCR. Therefore, when the telomerase reaction and PCR are both carried out as in the case of the reaction with the S7700 kit, it is necessary to ascertain that the material expected to inhibit the telomerase reaction does not generally inhibit PCR.

The S7700 kit includes a set of a template DNA and a primer for such ascertainment in the Primer Mix, and a 36-bp PCR amplification product is obtained from the set when the PCR is carried out.

Therefore, when the effect of a material expected to inhibit the telomerase reaction is verified using the S7700 kit, it is necessary to confirm that the telomerase reaction product is not detected in final results of electrophoresis, and that the 36-bp PCR product is normally amplified.

Comparative Example 1

In Comparative Example 1, the activity of telomerase attached to the S7700 kit was measured using the S7700 kit, as described above. The measurement procedure is as in the following.

First, in accordance with the protocol of the kit, a telomerase solution was prepared from the attached control cell pellet. Next, a reaction solution in a total volume of 20 µL was prepared by mixing 2 µL of 10×TRAP Reaction buffer, 0.4 µL of 50×dNTP Mix, 0.4 µL of TS primer, 0.4 µL of Primer Mix, 0.4 µL of TITANIUM Taq polymerase, 14.8 µL of milliQ water (purified water), and 1.6 µL of the telomerase solution prepared as described above.

Subsequently, the telomerase reaction was allowed by standing this reaction solution under a condition of 30° C. for 30 min. Thereafter, PCR was carried out by repeating 33 times a thermo cycle of: 30 sec at 94° C.; 30 sec at 59° C.; and 1 min at 72° C. With respect to the reaction solution after carrying out the PCR, an electrophoretic analysis was performed with Bioanalyzer 2100 (manufactured by Agilent Technologies Inc.).

Figure 4:
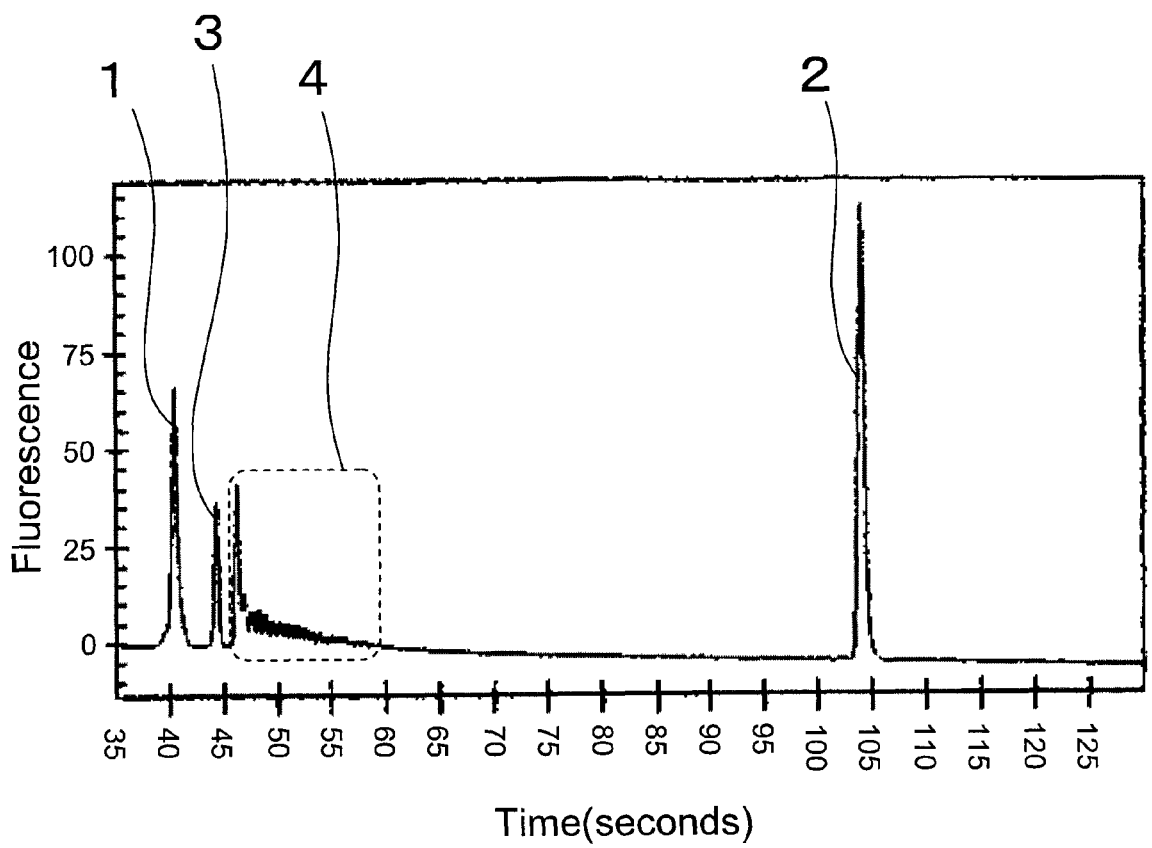
FIG. 4 shows a graph illustrating results of electrophoresis in Comparative Example 1.

FIG. 4 shows the results of the electrophoretic analysis.

Herein, peaks of Lower Marker denoted by a reference number "1" and Upper Marker denoted by a reference number "2" in FIG. 4 were provided for the internal control of the electrophoretic analysis for analyzing the length and the concentration of the electrophoresed sample DNA. Therefore, these were irrelevant to the results of the telomerase reaction and the PCR reaction described above.

On the other hand, the peak denoted by "PCR control" shows the 36-bp PCR amplification product obtained from the set of the template DNA and the primer included in the aforementioned Primer Mix.

Therefore, the peak was yielded with or without the telomerase reaction, and was a peak indicating whether or not the PCR reaction successfully proceeded. Still further, the remaining ladder peaks were yielded from DNA fragments having various lengths, which had been obtained by the telomerase reaction, by amplification according to the PCR reaction carried out thereafter. Therefore, the present Comparative Example 1 revealed that the telomerase reaction and the PCR reaction were both effected.

As a result of analysis with Bioanalyzer 2100, the DNA concentration in the reaction product corresponding to the PCR control peak was 1.23 ng/µL, and the total DNA concentration in the reaction product corresponding to the ladder peaks was 2.95 ng/µL.

Comparative Example 2

In Comparative Example 2, the telomerase activity attached to the S7700 kit was measured using the S7700 kit, in a similar manner to Comparative Example 1. However, upon the measurement, TMPyP was added to the reaction solution. Specifically, the experiment was carried out as follows.

Reaction solutions in a total volume of 20 µL were prepared by mixing 2 µL of 10×TRAP Reaction buffer, 0.4 µL of 50×dNTP Mix, 0.4 µL of TS primer, 0.4 µL of Primer Mix, 0.4 µL of TITANIUM Taq polymerase, 12.8 µL of milliQ water, 1.6 µL of the telomerase solution prepared in Comparative Example 1, and 2 µL of a TMPyP aqueous solution (the reaction solutions having final TMPyP concentrations of 0.01 µM, 0.03 µM, 0.1 µM, 0.3 µM, 1 µM, 3 µM and 10 µM were prepared, respectively).

Subsequently, in a similar manner to Comparative Example 1, the reaction solutions were stood under a condition of 30° C. for 30 min, followed by repeating 33 times the thermo cycle of: 30 sec at 94° C.; 30 sec at 59° C.; and 1 min at 72° C. With respect to the reaction solution after carrying out the PCR, an electrophoretic analysis was performed with Bioanalyzer 2100.

Example 1

In Example 1, the telomerase activity attached to the S7700 kit was measured using the S7700 kit, in a similar manner to Comparative Example 1. However, upon the measurement, CuPC was added to the reaction solution. Specifically, the experiment was carried out as follows.

Reaction solutions in a total volume of 20 µL were prepared by mixing 2 µL of 10×TRAP Reaction buffer, 0.4 µL of 50×dNTP Mix, 0.4 µL of TS primer, 0.4 µL of Primer Mix, 0.4 µL of TITANIUM Taq polymerase, 12.8 µL of milliQ water, 1.6 µL of the telomerase solution prepared in Comparative Example 1, and 2 µL of an aqueous CuPC solution (the reaction solutions having final CuPC concentrations of 0.01 µM, 0.03 µM, 0.1 µM, 0.3 µM, 1 µM, 3 µM and 10 µM were prepared, respectively).

Subsequently, in a similar manner to Comparative Example 1, the reaction solutions were stood under a condition of 30° C. for 30 min, followed by repeating 33 times the thermo cycle of: 30 sec at 94° C.; 30 sec at 59° C.; and 1 min at 72° C. With respect to the reaction solution after carrying out the PCR, an electrophoretic analysis was performed with Bioanalyzer 2100.

Example 2

In Example 2, the telomerase activity attached to the S7700 kit was measured using the S7700 kit, in a similar manner to Comparative Example 1. However, upon the measurement, NiPC was added to the reaction solution. Specifically, the experiment was carried out as follows.

Reaction solutions in a total volume of 20 µL were prepared by mixing 2 µL of 10×TRAP Reaction buffer, 0.4 µL of 50×dNTP Mix, 0.4 µL of TS primer, 0.4 µL of Primer Mix, 0.4 µL of TITANIUM Taq polymerase, 12.8 µL of milliQ water, 1.6 µL of the telomerase solution prepared in Comparative Example 1, and 2 µL of an aqueous NiPC solution (the reaction solutions having final NiPC concentrations of 0.01 µM, 0.03 µM, 0.1 µM, 0.3 µM, 1 µM, 3 µM and 10 µM were prepared, respectively).

Subsequently, in a similar manner to Comparative Example 1, the reaction solutions were stood under a condition of 30° C. for 30 min, followed by repeating 33 times the thermo cycle of: 30 sec at 94° C.; 30 sec at 59° C.; and 1 min at 72° C. With respect to the reaction solution after carrying out the PCR, an electrophoretic analysis was performed with Bioanalyzer 2100.

Example 3

In Example 3, the telomerase activity attached to the kit was measured using the S7700 kit, in a similar manner to Comparative Example 1. However, upon the measurement, PC was added to the reaction solution. Specifically, the experiment was carried out as follows.

Reaction solutions in a total volume of 20 µL were prepared by mixing 2 µL of 10×TRAP Reaction buffer, 0.4 µL of 50×dNTP Mix, 0.4 µL of TS primer, 0.4 µL of Primer Mix, 0.4 µL of TITANIUM Taq polymerase, 12.8 µL of milliQ water, 1.6 µL of the telomerase solution prepared in Comparative Example 1, and 2 µL of an aqueous PC solution (the reaction solutions having final PC concentrations of 0.01 µM, 0.03 µM, 0.1 µM, 0.3 µM, 1 µM, 3 µM and 10 µM were prepared, respectively).

Subsequently, in a similar manner to Comparative Example 1, the reaction solutions were stood under a condition of 30° C. for 30 min, followed by repeating 33 times the thermo cycle of: 30 sec at 94° C.; 30 sec at 59° C.; and 1 min at 72° C. With respect to the reaction solution after carrying out the PCR, an electrophoretic analysis was performed with Bioanalyzer 2100.

Figure 5:
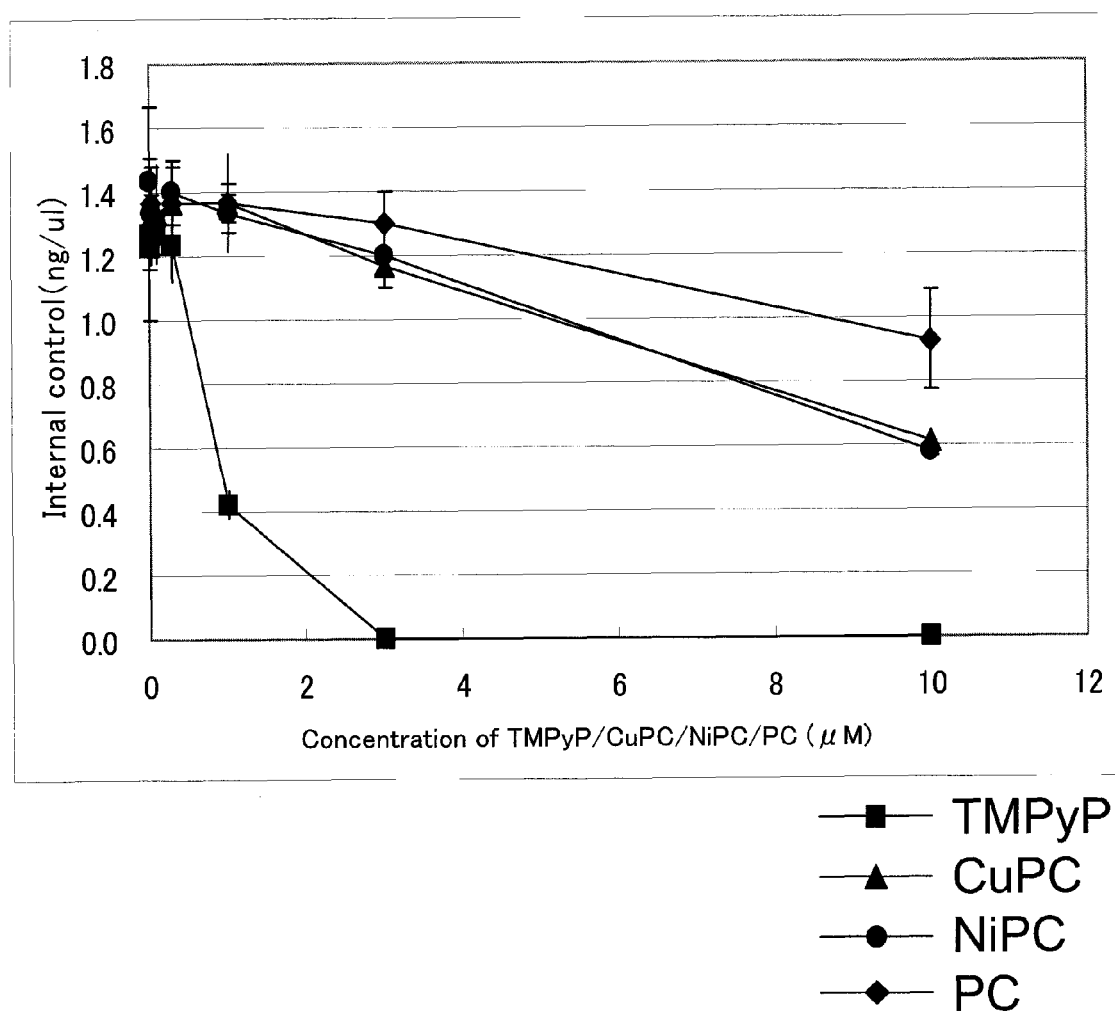
FIG. 5 shows a graph illustrating a relationship between the DNA concentrations corresponding to PCR control peaks and the concentrations of TMPyP or each anionic phthalocyanine in the reaction solution, based on each of the results of electrophoretic analyses of Comparative Examples 1 to 2 and Examples 1 to 3.

As in the foregoing, based on each of the results of electrophoretic analyses of Comparative Examples 1 to 2 and Examples 1 to 3, FIG. 5 shows a relationship between the DNA concentrations corresponding to the PCR control peaks and the concentrations of TMPyP or each anionic phthalocyanine in the reaction solution. More specifically, the relationship between the DNA concentrations corresponding to the PCR control peaks taken along the ordinate, and the concentrations of TMPyP or each anionic phthalocyanine in the reaction solution taken along the abscissa was plotted ("0" on the abscissa indicates the results of Comparative Example 1 not including any of each anionic phthalocyanine and TMPyP).

FIG. 5 has proven that the DNA concentration markedly decreased depending on the concentration of TMPyP, and the DNA concentrations in the range of the TMPyP concentration being not less than 3 µM was not beyond the detection limit of Bioanalyzer 2100.

That is, these results are believed to be due to the inhibition of general PCR reactions by TMPyP, because TMPyP would nonspecifically bind to the double-stranded DNA included as a template.

On the other hand, in the case of each anionic phthalocyanine, decrease in the DNA concentration was mild as compared with TMPyP, even when the concentration of the anionic phthalocyanine was 3 µM, the DNA of 1.1 ng/µL or more was detected. In other words, it is revealed that nonspecific binding to the double-stranded DNA by the anionic phthalocyanine is significantly weaker as compared to TMPyP.

Figure 6:
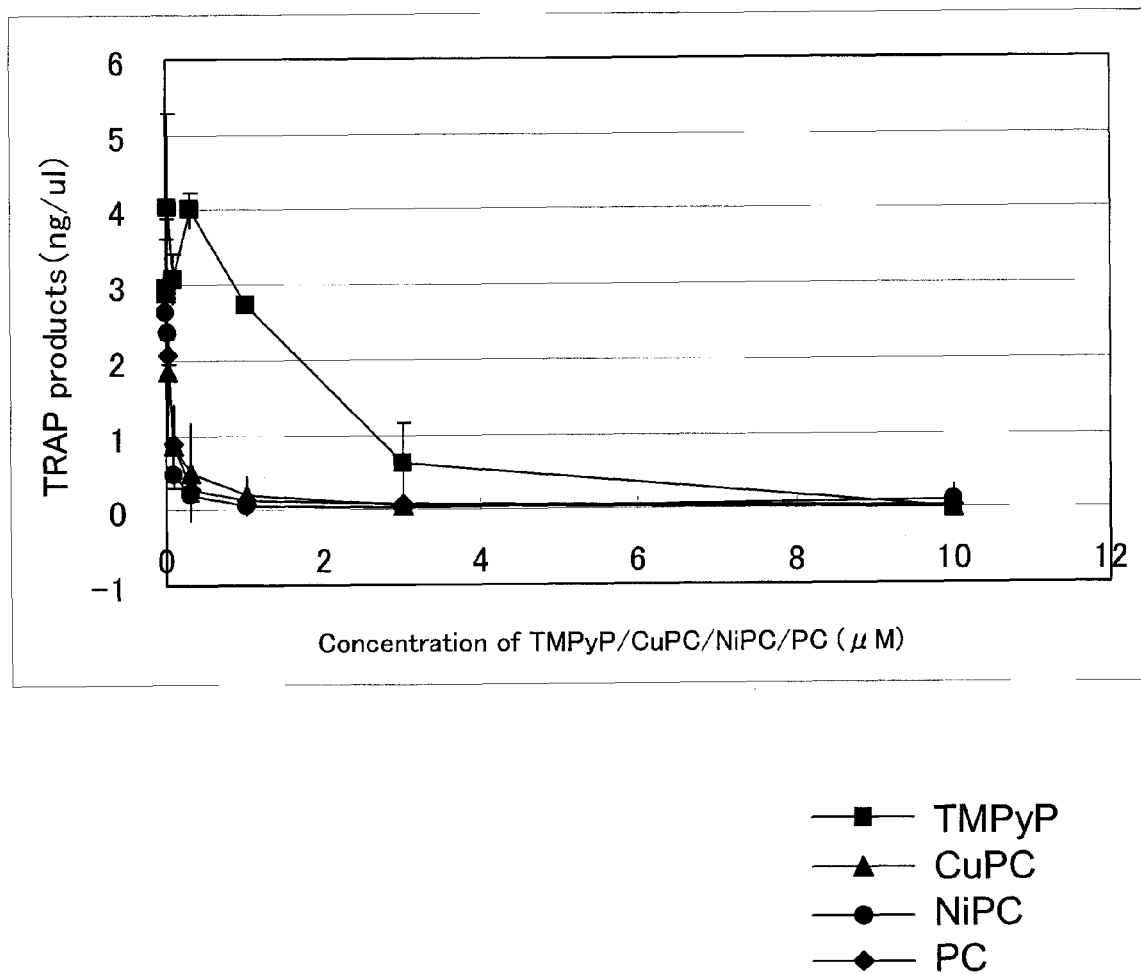
FIG. 6 shows a graph illustrating a relationship between total DNA concentrations corresponding to ladder peaks in the reaction product and the concentrations of TMPyP or each anionic phthalocyanine in the reaction solution, based on each of the results of electrophoretic analyses of Comparative Examples 1 to 2 and Examples 1 to 3.

Next, in FIG. 6, the relationship between the total DNA concentrations in the reaction product corresponding to ladder peaks taken along the ordinate and the concentrations of TMPyP or each anionic phthalocyanine in the reaction solution taken along the abscissa was plotted ("0" on the abscissa indicates the results of Comparative Example 1 not including any of TMPyP and each anionic phthalocyanine).

As shown in FIG. 6, in the case of each anionic phthalocyanine, the DNA concentration decreased depending on the concentration of each anionic phthalocyanine, and in the range of the each anionic phthalocyanine being not less than 0.1 µM, the DNA concentration was not greater than 1.0 ng/µL. On the other hand in the case of TMPyP, the total DNA concentration corresponding to the ladder peaks in the reaction product was 2.7 ng/µL even though 1.1 µM of TMPyP was added.

Accordingly, these results suggest that anionic phthalocyanines used in the present invention has evidently greater inhibitory effects on the telomerase reaction than TMPyP that is a cationic substance which has been conventionally known as a candidate inhibitor.

In brief, from the results of Comparative Examples 1 to 2 and Examples 1 to 3, it was revealed that anionic phthalocyanines have a more prominent effects of inhibiting a telomerase reaction and are less inhibitory to a DNA polymerase reaction as compared with TMPyP that is a cationic substance known as a conventional candidate inhibitor of a telomerase reaction.

Moreover, effects of inhibiting telomerase by TMPyP and anionic phthalocyanines were compared in Comparative Example 3 and Example 4 to 5 below. In these experiments, the S7700 kit was used similarly to the aforementioned Comparative Examples 1 to 2 and Examples 1 to 3. However, in Comparative Examples 1 to 2 and Examples 1 to 3 described above, the reagents required only for the telomerase reaction and PCR were all mixed first, and the telomerase reaction and PCR were carried out sequentially by regulating the reaction temperature. To the contrary, in the following Comparative Example 3 and Examples 4 to 5, only the reagents required for the telomerase reaction were first mixed to carry out a telomerase reaction, and a part of the reaction solution and the reagents required for the PCR were mixed to carry out the PCR.

In addition, in each of the following Comparative Example 3 and Examples 4 to 5, experiments were carried out with or without addition of a λDNA in the telomerase reaction. Addition of the λDNA was intended to reproduce for mimicking the conditions in which a large amount of double-stranded DNAs are present as in the case of genomic DNAs in cells, and to study the effects of inhibiting telomerase by TMPyP or anionic phthalocyanines even under conditions more approximate to those in vivo, by adding a λDNA.

Comparative Example 3

In Comparative Example 3, the inhibitory effect on the telomerase activity by TMPyP was studied using the S7700 kit. The measurement procedure is as in the following.

Telomerase reaction solution in a total volume of 10 µL were prepared by mixing 1 µL of 10×TRAP Reaction buffer, 0.2 µL of 50×dNTP Mix, 0.2 µL of TS primer, 4 µL of the telomerase solution prepared in Comparative Example 1, 2 µL of the TMPyP aqueous solution, and 2.6 µL of milliQ water (the reaction solutions having final TMPyP concentrations of 0 M, 0.1 µM, 0.3 µM, 1 µM, 3 µM and 10 µM were prepared, respectively). Then, the reaction solutions were stood under a condition of 30° C. for 60 min to allow a telomerase reaction to be carried out.

Next, 4 µL of a solution prepared by diluting the solution after the telomerase reaction 20 times with milliQ water, 0.2 µL of 50×dNTP Mix, 0.2 µL of TS primer, 0.2 µL of Primer Mix, 0.1 µL of TaKaLa LA Taq Hot Start Version (manufactured by Takara Bio Inc.), 1 µL of 10×LA PCR buffer II ($Mg^{2+}$ plus) (buffer solution included in TaKaLa LA Taq Hot Start Version), and 4.3 µL of milliQ water were mixed to prepare a PCR solution in a total volume of 10 µL. Then, PCR was carried out by allowing this PCR solution to stand under temperature conditions in which a thermo cycle of: 30 sec at 95° C.; 30 sec at 59° C.; and 30 sec at 72° C. was repeated 30 times.

Figure 16:
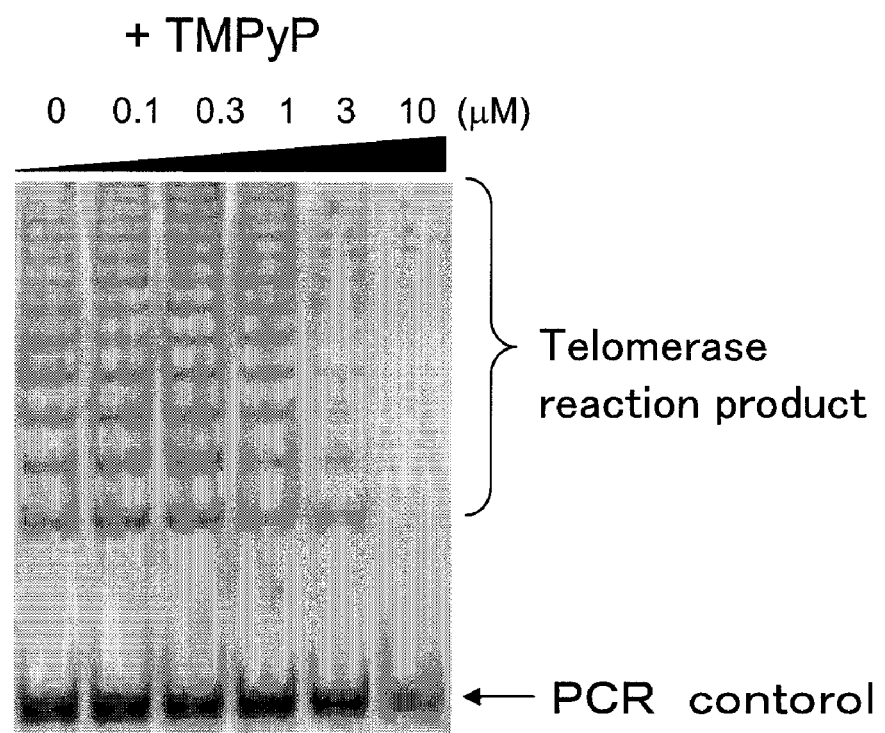
FIG. 16 shows results of gel electrophoresis demonstrating an effect of inhibiting telomerase by TMPyP in the absence of λDNA in Comparative Example 3.

Finally, the solution after the PCR was electrophoresed on a 10% polyacrylamide gel, and stained with GelStar Nucleic Acid Stain (manufactured by Takara Bio Inc.). FIG. 16 shows the results exhibited by the gel obtained as in the foregoing. In the order from the leftmost lane, the results with final concentrations of TMPyP being 0 M, 0.1 μM, 0.3 μM, 1 μM, 3 μM and 10 μM are shown. It is found that the band indicating the telomerase reaction product became weaker as the final concentration of TMPyP increased, revealing that TMPyP inhibited the telomerase reaction. However, under the condition in which 10 μM TMPyP was added, the band indicating the PCR control became weaker, revealing that the polymerase reaction was also inhibited.

Figure 17:
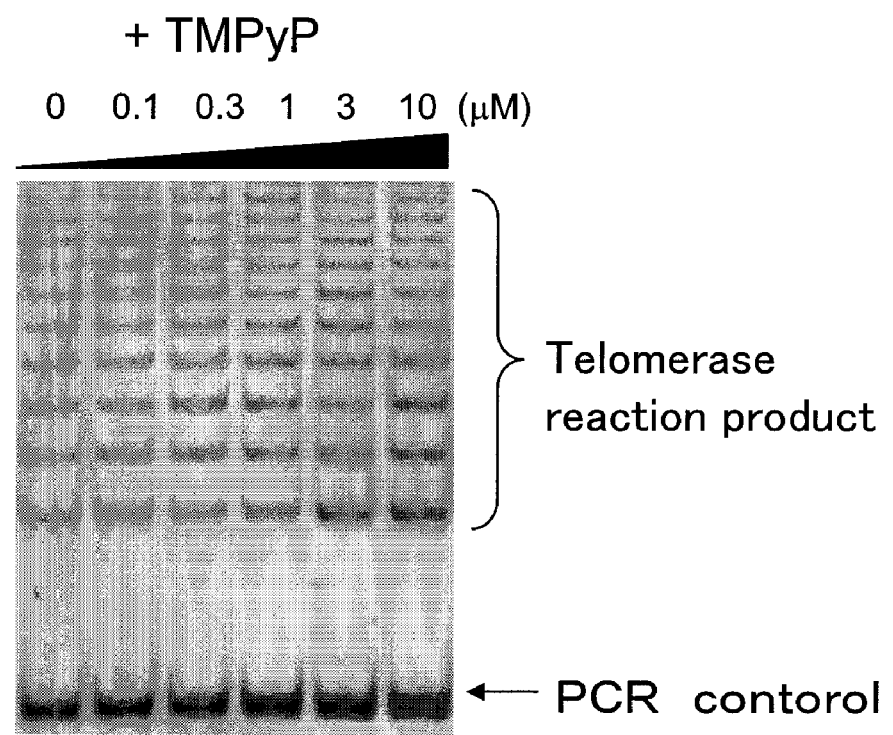
FIG. 17 shows results of gel electrophoresis demonstrating an effect of inhibiting telomerase by TMPyP in the presence of λDNA

On the other hand, experiments in which a λDNA was added to the telomerase reaction solution were also carried out. More specifically, in preparing the telomerase reaction solution described above, 2.6 μL of a λDNA solution (manufactured by Takara Bio Inc.) was mixed in place of mixing 2.6 μL of milliQ water. Other telomerase reaction temperature/time schedule, PCR solution preparation condition, PCR temperature/time schedule, electrophoresis condition were just the same. The results are shown in FIG. 17.

Accordingly, unlike FIG. 16, it is revealed that the telomerase reaction was not inhibited at all in the presence of the λDNA, even with higher concentrations of TMPyP. More specifically, it is revealed that under the conditions in which a large amount of double-stranded DNAs were present as in the case of genomic DNAs, the effect of inhibiting telomerase by TMPyP was markedly diminished.

Example 4

Figure 18:
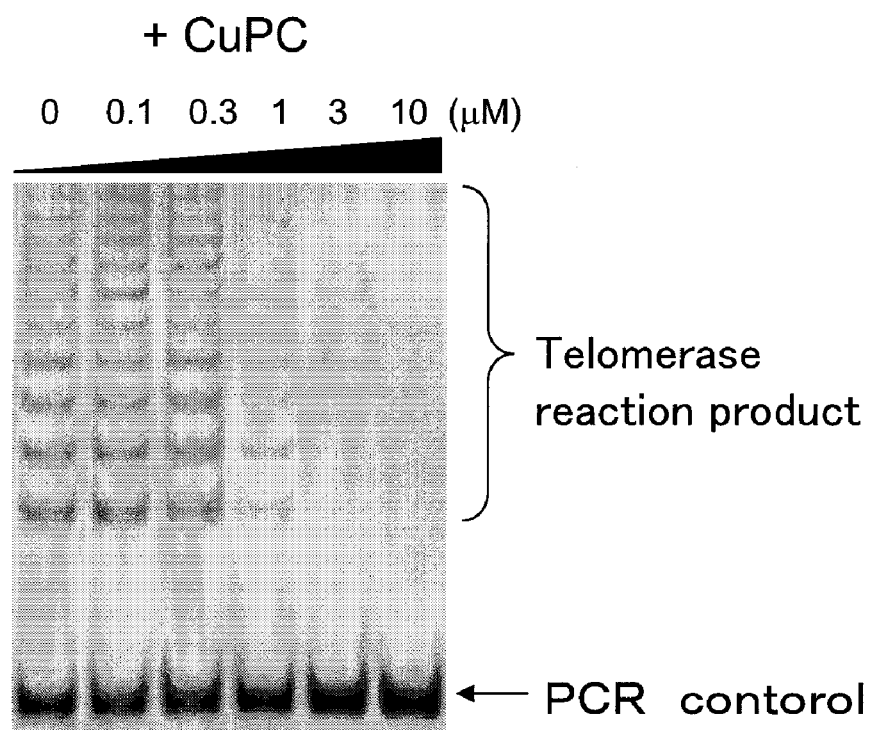
FIG. 18 shows results of gel electrophoresis demonstrating an effect of inhibiting telomerase by CuPC in the absence of λDNA in Example 4.
Figure 19:
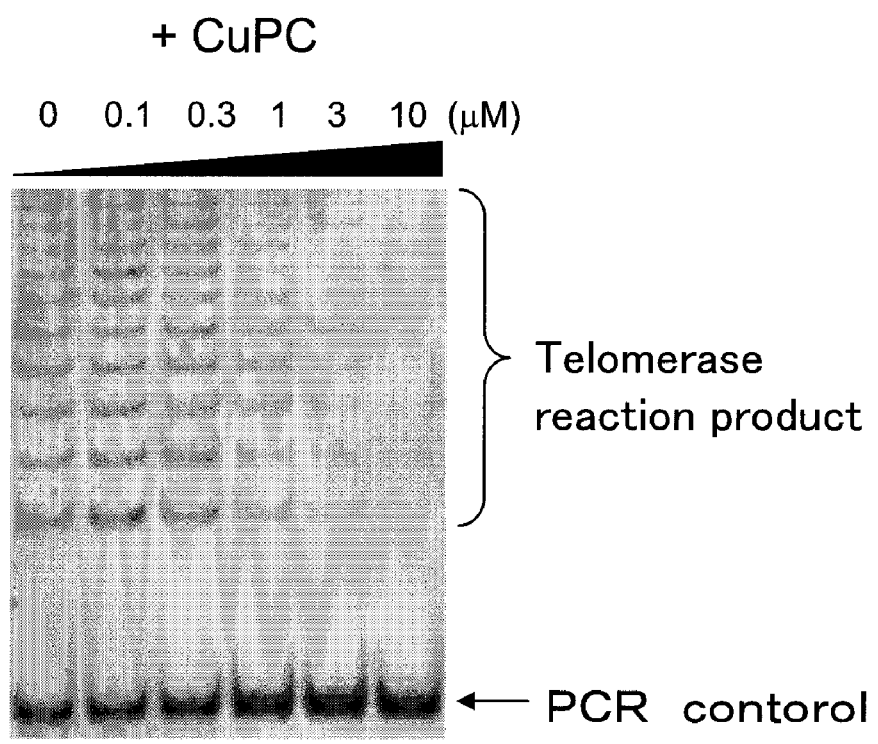
FIG. 19 shows results of gel electrophoresis demonstrating an effect of inhibiting telomerase by CuPC in the presence of λDNA in Example 4.

In Example 4, the experiment identical to Comparative Example 3 was carried out using CuPC in place of TMPyP. FIG. 18 and FIG. 19 show the results of the experiment. First, FIG. 18 shows the results under conditions with no addition of the λDNA, where in the order from the leftmost lane, the results with final concentrations of CuPC being 0 M, 0.1 μM, 0.3 μM, 1 μM, 3 μM and 10 μM are shown. It is revealed from the results that the telomerase reaction was inhibited with higher concentration of CuPC under the condition. Furthermore, unlike the case of TMPyP (FIG. 16), amplification of the PCR control was not inhibited even with 10 μM of CuPC.

On the other hand, FIG. 19 shows the results obtained in the presence of the λDNA. Accordingly, it is revealed that CuPC can efficiently inhibit the telomerase reaction even in the presence of the λDNA unlike the case of TMPyP. More specifically, it is revealed that even under the conditions in which a large amount of double-stranded DNAs are present as in the case of genomic DNAs, CuPC can exhibit the effect of inhibiting telomerase.

Example 5

Figure 20:
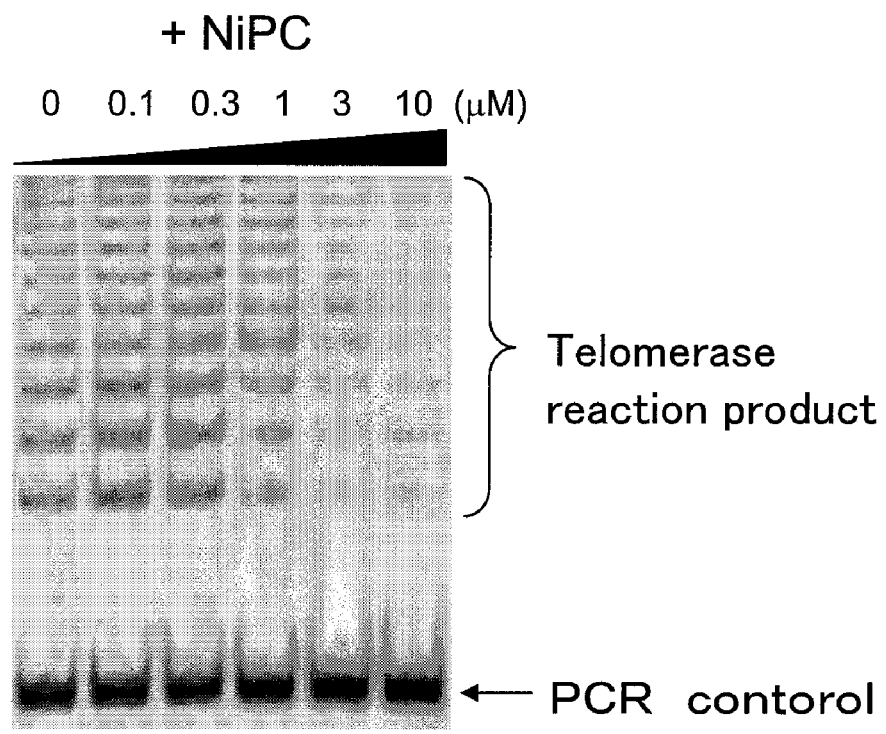
FIG. 20 shows results of gel electrophoresis demonstrating an effect of inhibiting telomerase by NiPC in the absence of λDNA in Example 5.
Figure 21:
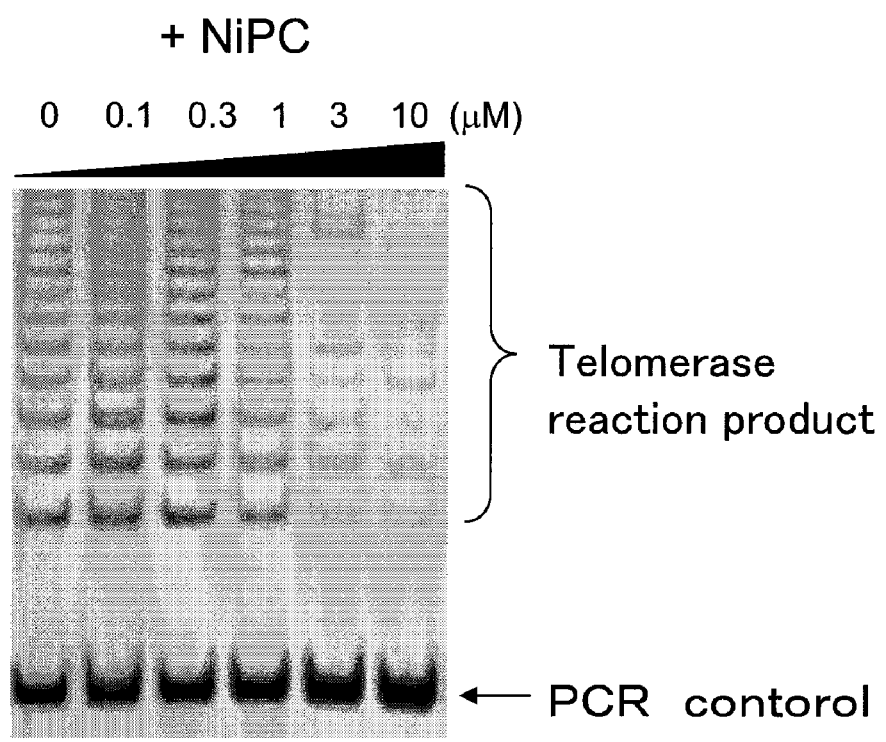
FIG. 21 shows results of gel electrophoresis demonstrating an effect of inhibiting telomerase by NiPC in the presence of λDNA in Example 6.

In Example 5, the experiment identical to Comparative Example 3 was carried out using NiPC in place of TMPyP. FIG. 20 and FIG. 21 show the results of the experiment. First, FIG. 20 shows the results under conditions with no addition of the λDNA, where in the order from the leftmost lane, the results with final concentrations of NiPC being 0 M, 0.1 μM, 0.3 μM, 1 μM, 3 μM and 10 μM are shown. It is revealed from the results that the telomerase reaction was inhibited with higher concentration of NiPC under the condition. Furthermore, unlike the case of TMPyP (FIG. 16), amplification of the PCR control was not inhibited even with 10 μM of NiPC.

On the other hand, FIG. 21 shows the results obtained in the presence of the λDNA. Accordingly, it is revealed that NiPC can efficiently inhibit the telomerase reaction even in the presence of the λDNA unlike the case of TMPyP. More specifically, it is revealed that even under the conditions in which a large amount of double-stranded DNAs are present as in the case of genomic DNAs, NiPC can exhibit the effect of inhibiting the telomerase reaction.

As in the foregoing, it was proven from the results of Comparative Example 3 and Examples 4 to 5 that CuPC and NiPC being anionic phthalocyanines can efficiently inhibit the telomerase reaction even under the conditions in which a large amount of double-stranded DNAs are present as in the case of genomic DNAs, unlike TMPyP that is a cationic substance which has been known as a conventional candidate inhibitor of a telomerase reaction.

—Study on Interaction between Anionic Phthalocyanine and Various DNAs—

Hereinafter, the interaction between anionic phthalocyanines and various DNAs was studied in Examples 6, 7, 8 and 9. For this purpose, a solution containing a G-quadruplex structure, a solution including a single-stranded DNA, and a solution containing a double-stranded DNA were first prepared according to the following procedures.

<Preparation of G-quadruplex Solution>

A solution of 50 mM HEPES and 100 mM NaCl, pH7 (total volume: 100 μL) containing a single-stranded DNA consisting of a sequence of 5'-gggttagggttagggttaggg-3' (SEQ ID NO: 2; this sequence being similar to a sequence of a human telomere portion, and thus the DNA referred to as "human telomeric oligo DNA" hereafter) was incubated at 90° C. for 5 min, and thereafter cooled to 0° C. at a rate of temperature fall of 2° C./min, followed by finally incubating at 0° C. for 2 hrs.

Figure 7:
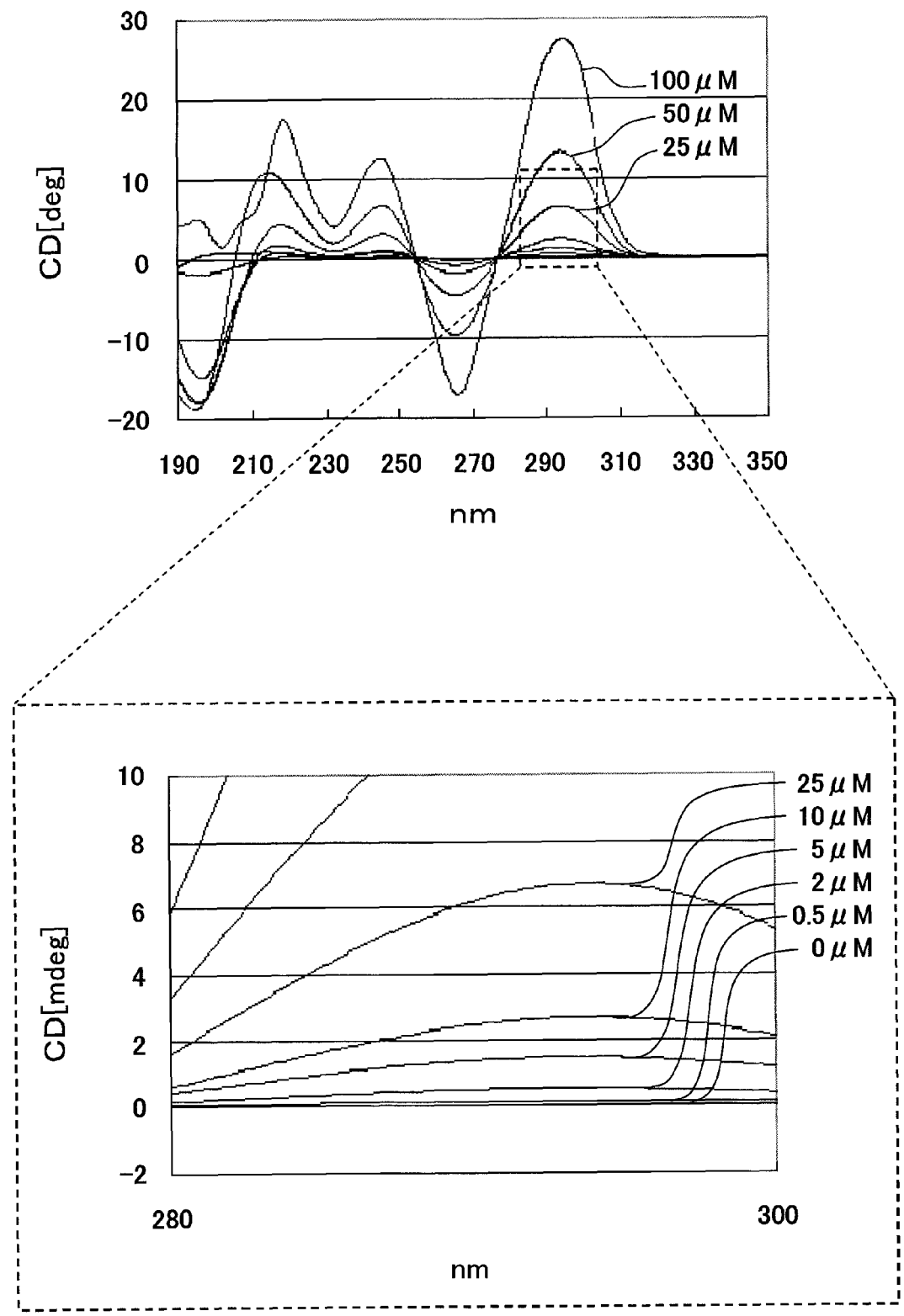
FIG. 7 shows a graph illustrating results of CD measurement demonstrating formation of an antiparallel G-quadruplex structure.

The concentrations of the human telomeric oligo DNA contained in the solution were 0, 0.5, 2, 5, 10, 25, 50 and 100 μM. As a result of CD analysis carried out on each solution after the preparation, a positive peak at around 295 nm, and a negative peak at around 265 nm were found in any of the cases as shown in FIG. 7, except for the case of a solution containing 0 μM human telomeric oligo DNA. This suggests that an antiparallel G-quadruplex was formed.

The absolute values of the positive and negative peaks were maximized for the solution having the human telomeric oligo DNA concentration of 100 μM, and dropped in the order of 50, 25, 10, 5, 2 and 0.5 μM. This suggests that when the concentration of the human telomeric oligo DNA contained first was high, the resultant concentration of the DNA forming the antiparallel G-quadruplex was also high. Hereafter, G-quadruplex solutions prepared from the solutions having human telomeric oligo DNA concentrations of 100, 50, 25, 10, 5, 2 and 0.5 μM are referred to as G-quadruplex solutions A, B, C, D, E, F and G, respectively. On the other hand, the solution without the human telomeric oligo DNA contained therein is referred to as NC solution.

<Preparation of Single-Stranded DNA Solution>

A solution of 50 mM HEPES and 100 mM NaCl, pH7 (total volume: 100 μL) containing a single-stranded DNA consisting of a sequence of 5'-tttttttttttttttttttt-3' sequence (SEQ ID NO: 3) at a concentration of 50 μM was prepared, which was incubated at 90° C. for 5 min, and thereafter cooled to 0° C. at a rate of temperature fall of 2° C./min, followed by finally incubating at 0° C. for 2 hrs. The DNA in thus resulting solution was a single-stranded DNA even after the incubation (hereafter, the solution referred to as "single-stranded DNA solution").

<Preparation of Double-Stranded DNA Solution>

A solution of 50 mM HEPES and 100 mM NaCl, pH7 (total volume: 100 μL) containing a single-stranded DNA consisting of a sequence of 5'-AGAAGAGAAAGA-3' (SEQ ID NO: 4) and a single-stranded DNA consisting of a sequence of 5'-TCTTTCTCTTCT-3' (SEQ ID NO: 5) at each concentration of 50 μM was prepared, which was incubated at 90° C. for 5 min, and thereafter cooled to 0° C. at a rate of temperature fall of 2° C./min, followed by finally incubating at 0° C. for 2 hrs. Since the aforementioned two kinds of DNAs are complementary to one another, both DNAs form a double-stranded DNA in the solution as a result of the incubation (hereafter, the solution referred to as "double-stranded DNA solution").

Example 6

In Example 6, the interaction between CuPC and various DNAs was studied.

First, a solution of 50 mM HEPES and 100 mM NaCl, pH7 (total volume: 20 μL) containing 15 μM CuPC was prepared. Then, this CuPC solution was mixed with each of the G-quadruplex solutions C, D, E and F and the NC solution, and the absorbance of these liquid mixtures were measured at 480 to 800 nm.

Figure 8:
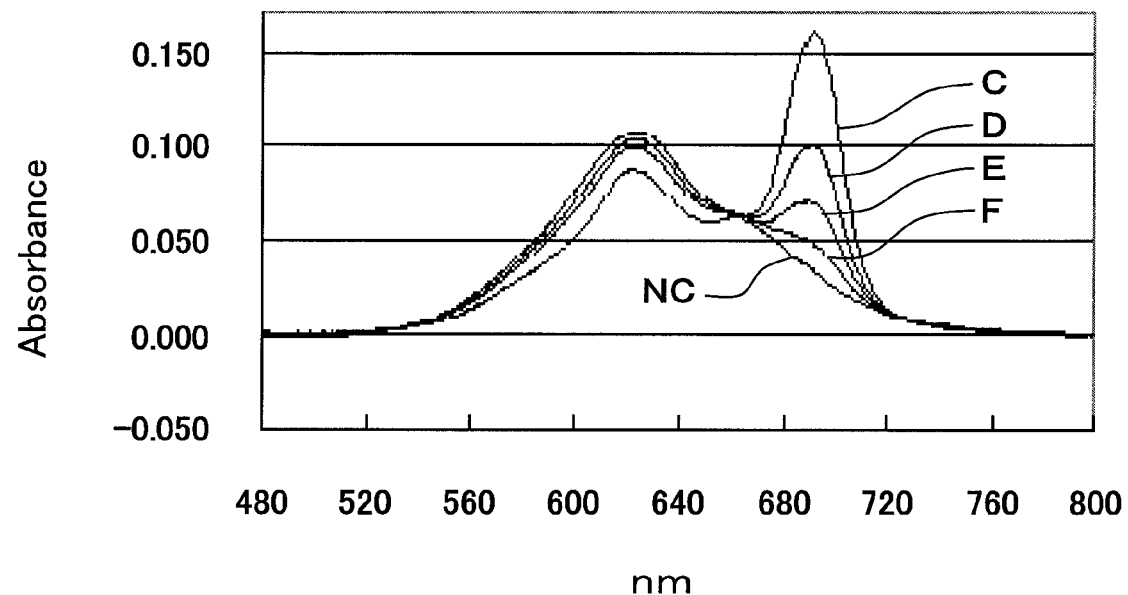
FIG. 8 shows a graph illustrating an absorption spectrum at 480 nm to 800 nm when CuPC and a G-quadruplex structure were mixed in Example 4.

FIG. 8 shows the measurement results. It is revealed from FIG. 8 that a peak appeared in the range of approximately 640 to 720 nm except for the case of NC solution not containing a DNA, and these peaks were intense in the order of the G-quadruplex solutions C>D>E>F. From the foregoing results, it is revealed that an interaction occurred between CuPC and the G-quadruplex structure.

Figure 9:
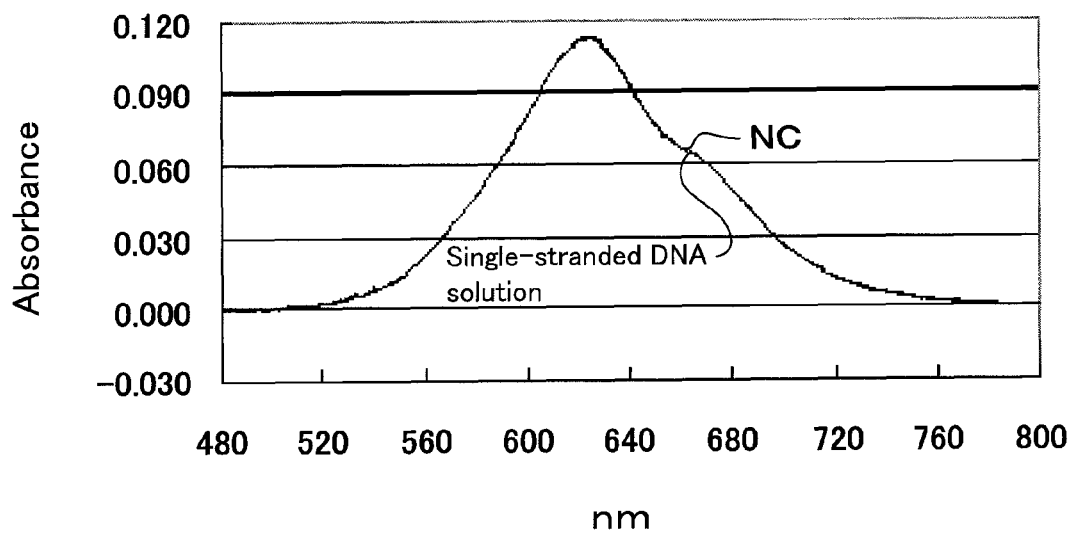
FIG. 9 shows a graph illustrating an absorption spectrum at 480 nm to 800 nm when CuPC and a single-stranded DNA (A), or CuPC and a double-stranded DNA (B) were mixed in Example 4.
Figure 9:
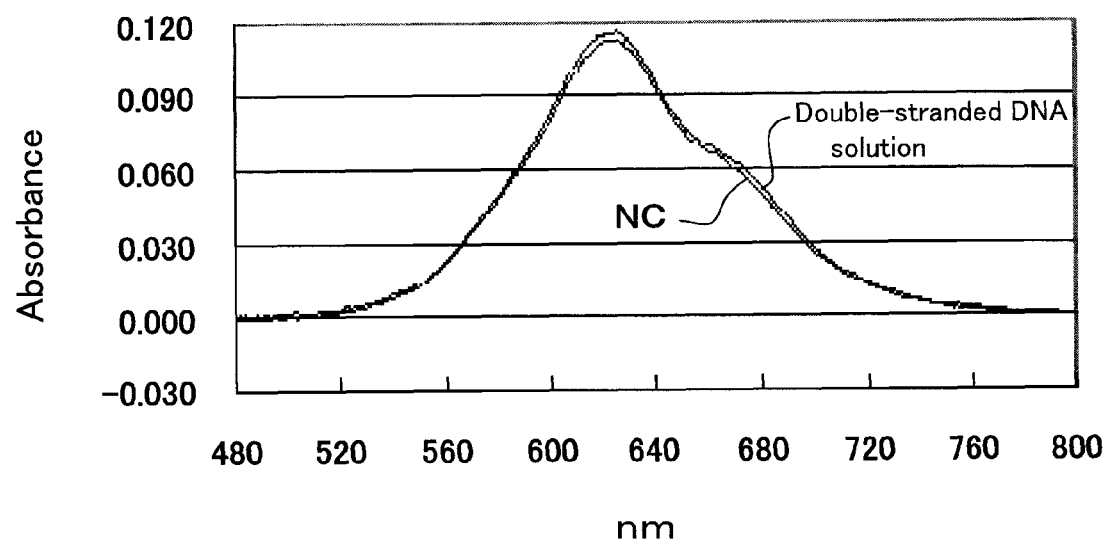

Next, the aforementioned CuPC solution and single-stranded DNA solution, and the aforementioned CuPC solution and double-stranded DNA solution were similarly mixed, respectively. And then the absorbance of these liquid mixtures was measured at 480 to 800 nm. FIG. 9(A) and FIG. 9(B) show the results of the measurement in the cases of the single-stranded DNA solution and the double-stranded DNA solution, respectively.

In each drawing, the result obtained when the NC solution was used is also shown together. It is revealed from FIG. 9(A) and FIG. 9(B) that in both cases of the single-stranded DNA solution and the double-stranded DNA solution, the results which were almost the same as the case of the NC solution were obtained despite that the DNA was contained at a concentration as high as 50 μM. Therefore, it is revealed that an interaction did not occur between CuPC and the single-stranded DNA, and CuPC and the double-stranded DNA.

Example 7

In Example 7, the interaction between NiPC and various DNAs was studied.

First, a solution of 50 mM HEPES and 100 mM NaCl, pH7 (total volume: 20 μL) containing 15 μM NiPC was prepared. Then, this NiPC solution was mixed with each of the G-quadruplex solutions D, E, F and G, and the NC solution, and the absorbance of these liquid mixtures were measured at 480 to 800 nm.

Figure 10:
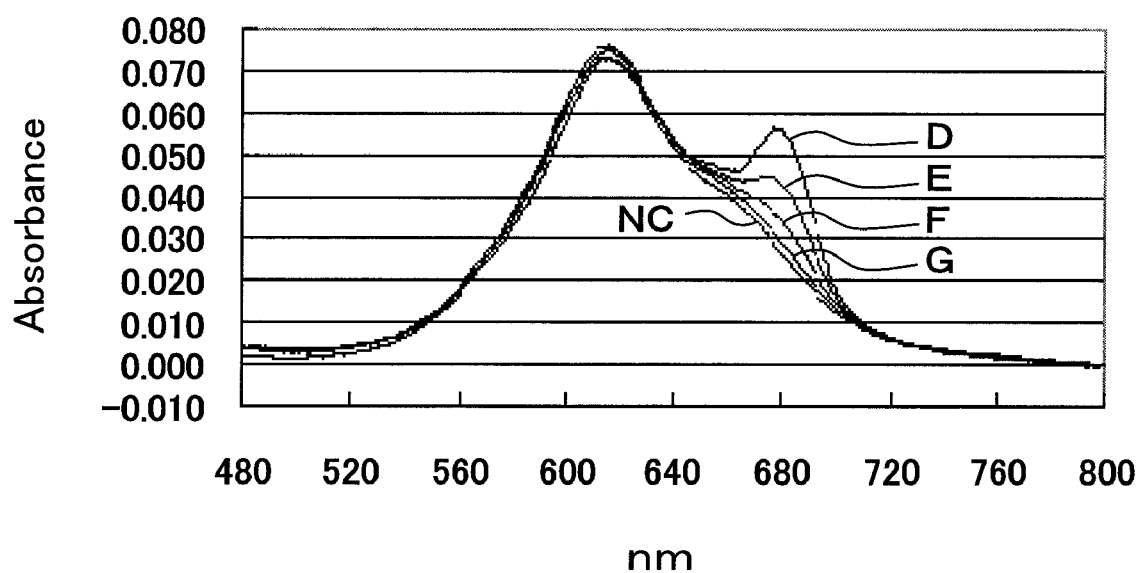
FIG. 10 shows a graph illustrating an absorption spectrum at 480 nm to 800 nm when NiPC and a G-quadruplex structure were mixed in Example 5.

FIG. 10 shows the measurement results. It is revealed from FIG. 10 that a peak appeared in the range of approximately 640 to 720 nm except for the case of NC solution not containing a DNA, and these peaks were intense in the order of the G-quadruplex solutions D>E>F>G. From the foregoing results, it is revealed that an interaction occurred between NiPC and the G-quadruplex structure.

Figure 11:
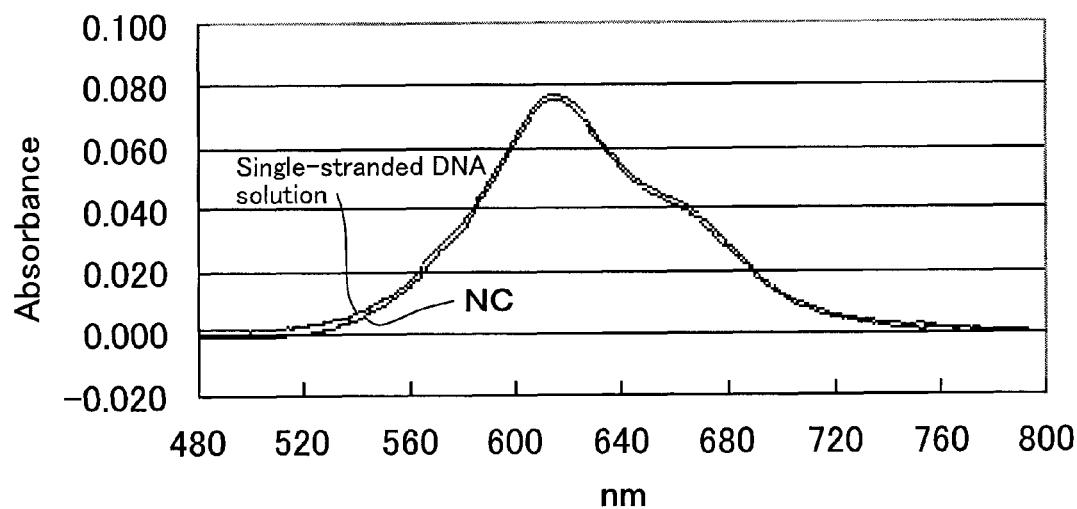
FIG. 11 shows a graph illustrating an absorption spectrum at 480 nm to 800 nm when NiPC and a single-stranded DNA (A), or NiPC and a double-stranded DNA (B) were mixed in Example 5.
Figure 11:
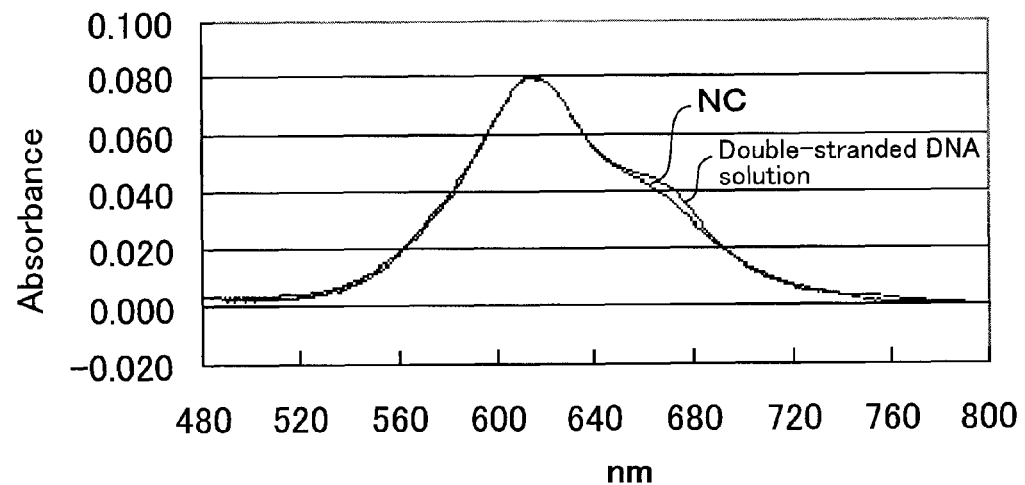

Next, the aforementioned NiPC solution and single-stranded DNA solution, and the aforementioned NiPC solution and double-stranded DNA solution were similarly mixed, respectively; the absorbance of these liquid mixtures was measured at 480 to 800 nm. FIG. 11(A) and FIG. 11(B) show the results of the measurement in the cases of the single-stranded DNA solution and the double-stranded DNA solution, respectively. In each drawing, the result obtained when the NC solution was used is also shown together. It is revealed from FIG. 11(A) and FIG. 11(B) that in both cases of the single-stranded DNA solution and the double-stranded DNA solution, the results which were almost the same as the case of the NC solution were obtained despite that the DNA was contained at a concentration as high as 50 μM. Therefore, it is revealed that an interaction did not occur between NiPC and the single-stranded DNA, and NiPC and the double-stranded DNA.

Example 8

In Example 8, the interaction between PC and various DNAs was studied.

First, a solution of 50 mM HEPES and 100 mM NaCl, pH7 (total volume: 20 μL) containing 15 μM PC was prepared. Then, this PC solution was mixed with each of the G-quadruplex solutions D, E, F and G, and the NC solution, and the absorbance of these liquid mixtures were measured at 480 to 800 nm.

Figure 12:
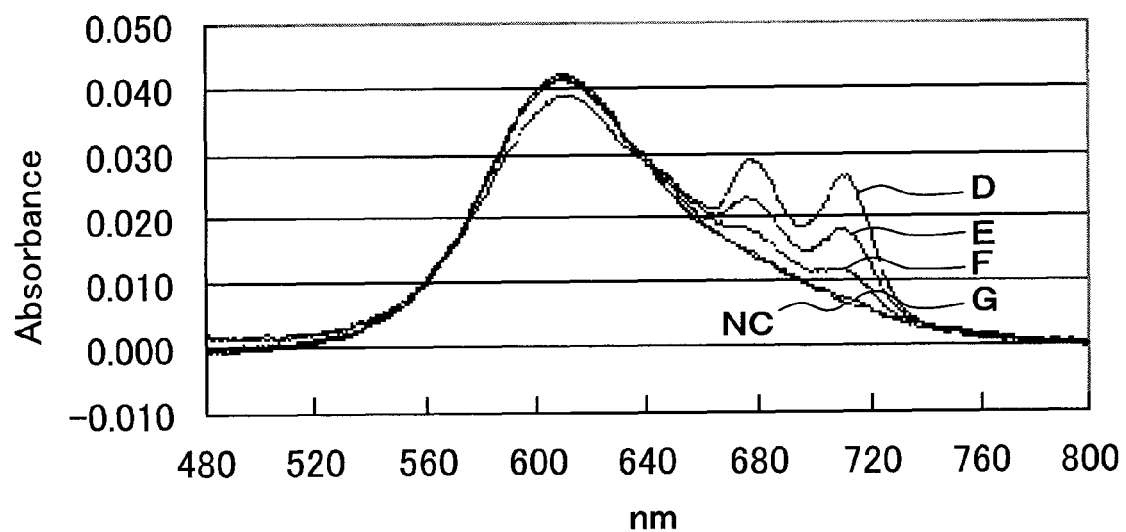
FIG. 12 shows a graph illustrating an absorption spectrum at 480 nm to 800 nm when PC and a G-quadruplex structure were mixed in Example 6.

FIG. 12 shows the measurement results. It is revealed from FIG. 12 that two peaks appeared in the range of 660 to 740 nm except for the case of NC solution not containing a DNA, and these peaks were intense in the order of the G-quadruplex solutions D>E>F>G. From the foregoing results, it is revealed that an interaction occurred between PC and the G-quadruplex structure.

Figure 13:
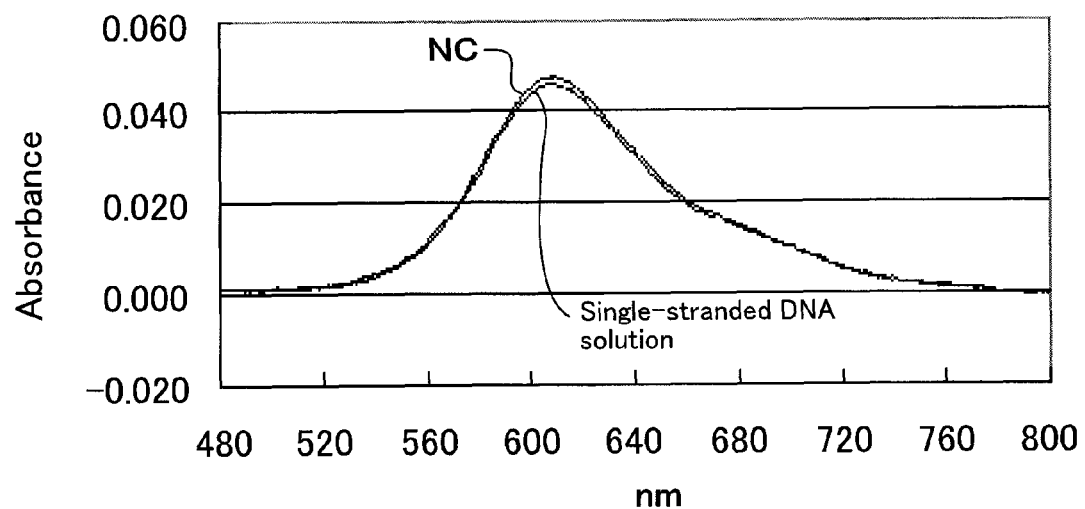
FIG. 13 shows a graph illustrating an absorption spectrum at 480 nm to 800 nm when PC and a single-stranded DNA (A), or PC and a double-stranded DNA (B) were mixed in Example 6.
Figure 13:
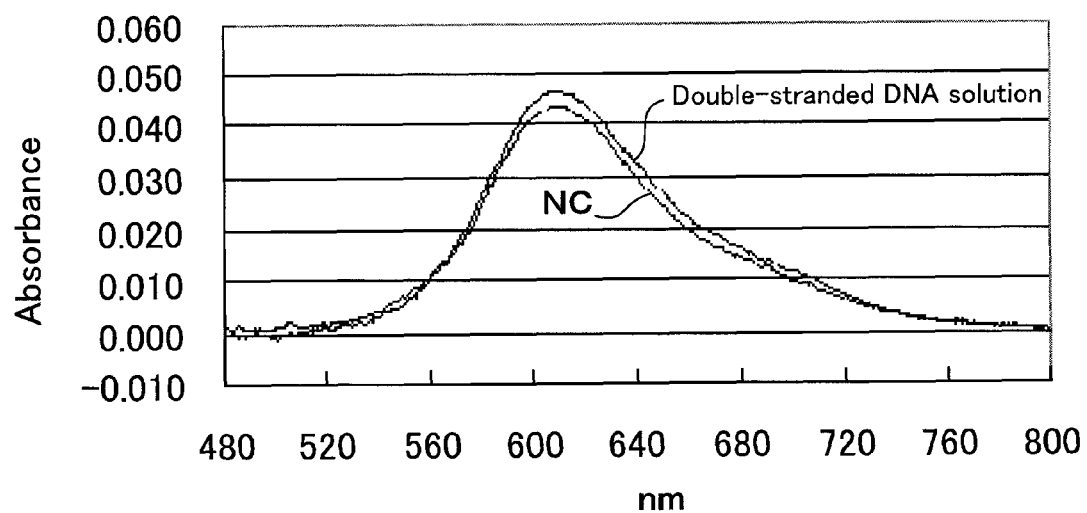

Next, the aforementioned PC solution and single-stranded DNA solution, and the aforementioned PC solution and double-stranded DNA solution were similarly mixed, respectively; the absorbance of these liquid mixture was measured at 480 to 800 nm. FIG. 13(A) and FIG. 13(B) show the results of the measurement in the cases of the single-stranded DNA solution and the double-stranded DNA solution, respectively. In each drawing, the result obtained when the NC solution was used is also shown together. It is revealed from FIG. 13(A) and FIG. 13(B) that in both cases of the single-stranded DNA solution and the double-stranded DNA solution, the results which were almost the same as the case of the NC solution were obtained despite that the DNA was contained at a concentration as high as 50 μM. Therefore, it is revealed that an interaction did not occur between PC and the single-stranded DNA, and PC and the double-stranded DNA.

Example 9

In Example 9, the interaction between CoPC and various DNAs was studied.

First, a solution of 50 mM HEPES and 100 mM NaCl, pH7 (total volume: 20 μL) containing 15 μM CoPC was prepared. Then, this CoPC solution was mixed with each of the G-quadruplex solutions B, C, D and G, and the NC solution, and the absorbance of these liquid mixtures were measured at 480 to 800 nm.

Figure 14:
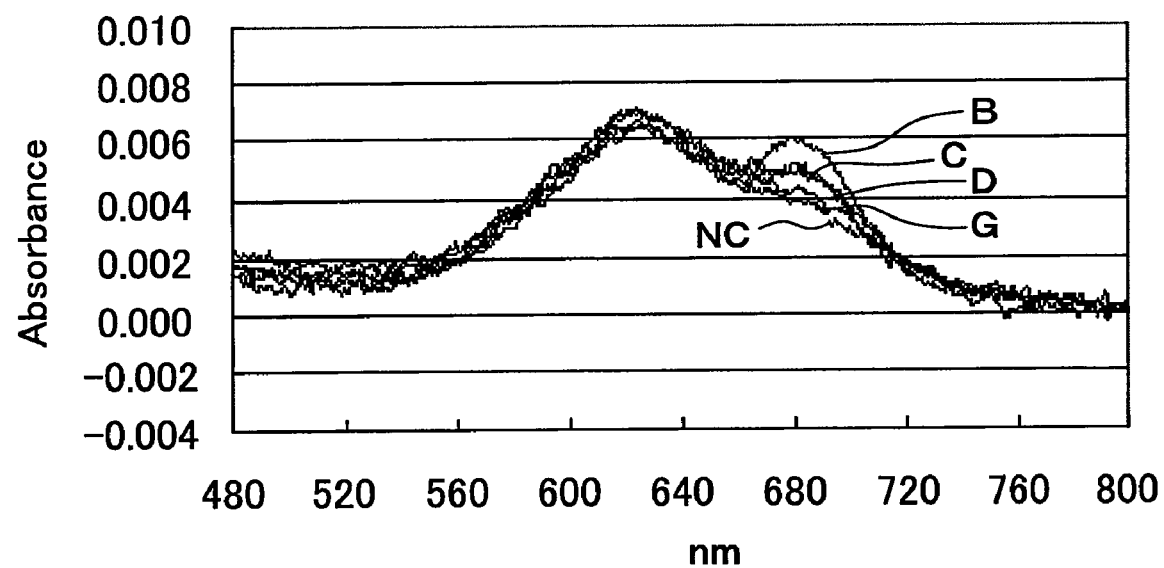
FIG. 14 shows a graph illustrating an absorption spectrum at 480 nm to 800 nm when CoPC and a G-quadruplex structure were mixed in Example 7.

FIG. 14 shows the measurement results. It is revealed from FIG. 14 that two peaks appeared in the range of 660 to 740 nm except for the case of NC solution not containing a DNA, and these peaks were intense in the order of the G-quadruplex solutions B>C>D>G. From the foregoing results, it is revealed that an interaction occurred between CoPC and the G-quadruplex structure.

Meanwhile, elevation of the peaks in the range of 640 to 720 nm observed when CoPC was used was less than the resultant elevation when CuPC, NiPC or PC was used. Such findings were presumed to the result from insufficient purification of the synthesized CoPC.

Figure 15:
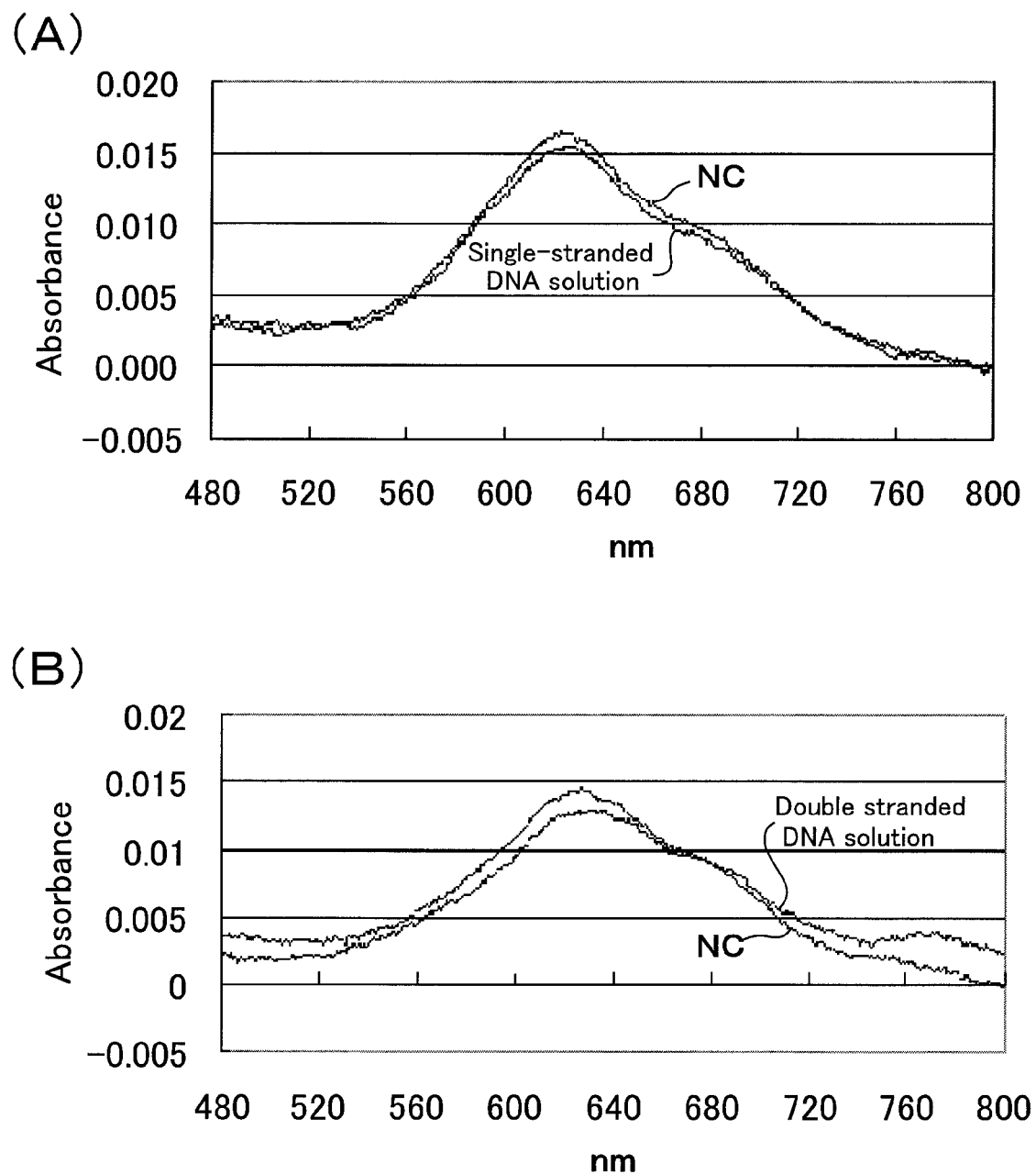
FIG. 15 shows a graph illustrating an absorption spectrum at 480 nm to 800 nm when CoPC and a single-stranded DNA (A), or CoPC and a double-stranded DNA (B) were mixed in Example 7.

Next, the aforementioned CoPC solution and single-stranded DNA solution, and the aforementioned CoPC solution and double-stranded DNA solution were similarly mixed, respectively, and then the absorbance of these liquid mixtures was measured at 480 to 800 nm. FIG. 15(A) and FIG. 15(B) show the results of the measurement in the cases of the single-stranded DNA solution and the double-stranded DNA solution, respectively. In each drawing, the result obtained when the NC solution was used is also shown together. It is revealed from FIG. 15(A) and FIG. 15(B) that in both cases of the single-stranded DNA solution and the double-stranded DNA solution, the results which were almost the same as the case of the NC solution were obtained despite that the DNA was contained at a concentration as high as 50 µM. Therefore, it is revealed that an interaction did not occur between CoPC and the single-stranded DNA, and CoPC and the double-stranded DNA.

In addition to the anionic phthalocyanine as described above, it was shown that as a result of a similar experiment carried out using ZnPC, ZnPC also specifically interacted with a G-quadruplex structure.

In summary of Examples 6 to 9 described above, it was proven that although any of the anionic phthalocyanine interacted with a G-quadruplex structure, it was extremely specific, and the interaction with a single-stranded DNA or a double-stranded DNA did not occur. Therefore, it is concluded that anionic phthalocyanines are very suitable as telomerase inhibitors, and the method for inhibiting telomerase according to the present invention is more effective as compared with conventional methods.

From the description hereinabove, many modifications and other embodiments of the present invention are apparent to persons skilled in the art. Accordingly, the foregoing description should be construed merely as an illustrative example, which was provided for the purpose of teaching best modes for carrying out the present invention to persons skilled in the art. Details of the construction and/or function of the present invention can be substantially altered without departing from the spirit thereof.

[Industrial Applicability]

The present invention provides a method for inhibiting telomerase. Since a telomerase reaction has been known to be the cause of malignant transformation, the method of the present invention can be used in treatment of cancer.

Reference Signs List

1 Lower Marker
2 Upper Marker
3 Peak of PCR control
4 Ladder peak

The invention claimed is:

1. A method for inhibiting a DNA extension reaction by telomerase, the method comprising:
    adding an anionic phthalocyanine to a solution containing telomerase, an anionic DNA to be a substrate of a telomerase reaction, and dNTPs so as to inhibit the DNA extension reaction by telomerase,
    wherein, the anionic phthalocyanine has at least one functional group selected from the group consisting of a sulfo group and a metal salt of a sulfo group.

2. The method according to claim 1, wherein the solution is a buffer solution.

3. The method according to claim 1, wherein the anionic phthalocyanine is either an anionic phthalocyanine having copper, zinc, cobalt or nickel as a coordination metal, or an anionic phthalocyanine not having a coordination metal.

* * * * *